United States Patent [19]
Baum et al.

[11] Patent Number: 5,858,744
[45] Date of Patent: Jan. 12, 1999

[54] RETROVIRAL VECTOR HYBRIDS AND THE USE THEREOF FOR GENE TRANSFER

[75] Inventors: Christopher Baum; Carol Stocking-Harbers; Wolfram Ostertag, all of Hamburg, Germany

[73] Assignee: Boehringer Mannheim GmbH, Mannheim, Germany

[21] Appl. No.: 793,610

[22] PCT Filed: Aug. 10, 1995

[86] PCT No.: PCT/EP95/03175

§ 371 Date: Mar. 7, 1997

§ 102(e) Date: Mar. 7, 1997

[87] PCT Pub. No.: WO96/07747

PCT Pub. Date: Mar. 14, 1996

[30] Foreign Application Priority Data

Sep. 8, 1994 [DE] Germany .......................... 44 31 973.8
Feb. 7, 1995 [DE] Germany ........................ 195 03 952.1

[51] Int. Cl.$^6$ ........................... C12N 15/11; C12N 15/63; C12N 5/10
[52] U.S. Cl. .................................... 435/172.3; 435/320.1; 435/366; 435/372; 435/372.1
[58] Field of Search ............................. 435/69.1, 172.1, 435/172.3, 320.1, 329, 366, 371, 372, 372.1, 372.2, 372.3; 424/93.2, 93.6

[56] References Cited

PUBLICATIONS

Verma et al., Nature, vol. 389, pp. 239–242, Sep. 18, 1997.
Orkin et al., "Report and Recommendations of the Panel to Assess the NIH Investment in Research on Gene Therapy", Dec. 7, 1995.
Chatis et al., *Proc. Natl. Acad. Sci.*, vol. 80 (Jul.) 1983, pp. 4408–4411, "Role for the 3' end of the genome in the determining disease specificity of Friend and Moloney murine leukemia virus".
Grez et al., *Proc. Natl. Acad. Sci.*, vol. 87 (Dec.) 1990, pp. 9202–9206, "Embryonic stem cell virus, a recombinant murine retrovirus with expression in embryonic stem cells".
Li et al., *J. Virology*, vol. 61, No. 3 (Mar.) 1987, pp. 693–700, "Disease specificity of non–defective Friend and Moloney murine leukemia viruses . . . ".
Velu et al., Cohen–Haguenauer and Boiron (ed.), *Colloque INSERM (Institut National de la Sante et de la Recherche Medicale)*, vol. 219 (1991) pp. 273–274, "Highly efficient retroviral vectors derived form Harvey and Friend murine viruses".
International Publication WO 94/09120 published 28 Apr. 1994.
International Publication WO 94/13824 published 23 Jun. 1994.
Stocking et al., Doerfler and Boehm (ed.), *Virus Strategies, Molecular Biology and Pathogenesis* 1993, pp. 433–455, "Regulation of retrovirus infection and expression in embryonic and hematopoietic stem cells".
Loh et al., *Mol. Cell. Biol.*, vol. 10, No. 8 (Aug.) 1990, pp. 4045–4057, "Evidence for a stem cell–specific repressor of Moloney murine leukemia virus expression in embryonal . . . ".
Valerio et al., *Gene*, vol. 84, 1989, pp. 419–427, "Retrovirus–mediated gene transfer into embryonal carcinoma and hemopoietic stem cells: expression from a hybrid long terminal repeat".
Akgün et al., *J. Virology*, vol. 65, No. 1, (Jan.) 1991, pp. 382–388, "Determinants of retrovirus gene expression in embryonal carcinoma cells".
Couture et al., *Human Gene Therapy*, vol. 5, No. 6 (Jun.) 1994, pp. 667–677, "Retroviral vectors containing chimeric promoter/enhancer elements exhibit cell–type–specific gene expression".
Beck–Engeser et al., *Human Gene Therapy*, vol. 2, No. 1, 1991, pp. 61–70, "Retroviral vectors related to the Myeloproliferative sarcoma virus allow efficient expression in hematopoietic stem and . . . ".
Gonda et al., *J. Virology*, vol. 51, No. 2, (Aug.) 1984, pp. 306–314, "Heteroduplex analysis of molecular clones of the pathogenic Friend virus complex . . . ".
Ahlers et al., *J. Virology*, vol. 68, No. 11, (Nov.) 1994, pp. 7235–7243, "Selectable retrovirus vector encoding Friend virus gp55 or erythropoietin induce . . . ".
Ostertag et al., 24th Annual Meeting of the International Society for Experimental Hematology, Aug. 27–31, 1995, *Experimental Hematology* (Charlottesville) 23 (8), (Aug. 30) 1995, 841, Abstract No. 344 "Novel and efficient retroviral vectors for somatic gene therapy and for stem cell protection.".
Velu et al., *Science*, vol. 238 (Dec. 4) 1987, pp. 1408–1410, "Epidermal growth factor–dependent transformation by a human EGF receptor proto–oncogene".
Velu et al., *J. Virology*, vol. 63, No. 3, (Mar.) 1989, pp. 1384–1392, "Harvey murine sarcoma virus: Influences of coding and noncoding sequences on cell transformation . . . ".

*Primary Examiner*—David Guzo
*Attorney, Agent, or Firm*—Nikaido Marmelstein Murray & Oram LLP

[57] ABSTRACT

Replication-defective retroviral vector hybrids which are characterized in that they contain a) the U5 region and/or tRNA primer binding site of MESV as the U5 region and/or tRNA primer binding site in the leader region and b) the U3 and R regions from a Friend murine leukaemia virus (F-MuLV) as the U3 and R regions in the 3'-LTR and which are particularly suitable for an effective gene transfer in haematopoietic stem cells.

26 Claims, 14 Drawing Sheets

K-562

TF-1

RETROVIRAL VECTOR HYBRIDS AND THE USE THEREOF FOR GENE TRANSFER

This application is a 371 of PCT/EP95/03175, filed Aug. 10, 1995.

The invention concerns retroviral vector hybrids and their use for gene transfer in particular for gene transfer into haematopoietic stem cells (ES).

Retroviral vectors with replication defects are at present a standard in gene transfer and gene therapy applications on cells of the human blood-forming system (A. D. Miller (1992) (1), R. C. Mulligan (1993) (2), R. Vile and S. J. Russell (1994) (3)). Their main advantages are:

- the infection leads to a stable integration of the vector and of the DNA sequences transferred by it into the host genome of mitotically active cells
- the number of integrations into the host genome can be controlled via the infection conditions
- the safety aspects of retroviral gene transfer are well researched; complications have so far not occurred in numerous applications on humans.

The most frequently cited advantage of retroviral vectors, their high gene transfer efficiency, only partly applies to applications on the blood-forming system. Only late maturing blood-forming precursor cells can preferably be infected with conventional vectors based on the Moloney murine sarcoma virus (MoMuSV); 30–95% of the precursor cells transduced with these vectors exhibit either no or an inadequate expression of the transferred genes due to primary silencing mechanisms (4); moreover after a longer residence period in vivo the retrovirally controlled gene expression is weakened in a high percentage of the initially expressing cells up to the point of non-function due to secondary silencing (Palmer et al. (1991) (5), Brenner et al. (1993) (6)).

It has been demonstrated that also in embryonic cells such as embryonic carcinoma cells (myeloid (non-lymphatic) derivatives of haematopoietic stem cells) the viruses are indeed integrated but the expression of the integrated provirus is blocked.

Mutations and derivatives of MoMuSV are known from Stocking et al. (1993) (21) which can be used to improve the retroviral gene expression in such cells. Such hybrids are obtained by point mutations in the LTRs especially in the U3 region. For example the binding of the ECF-1 repressor can be reduced by a point mutation at −345 of MoMuLV. A point mutation which creates a binding site for SP-1 (e.g. point mutation at −166 (S. McKnight and R. Tijan (1986) (16)) is equally advantageous. It is furthermore advantageous to also introduce mutations outside the LTR regions. It has been shown that an 18 bp region which adjoins the 5'-LTR directly downstream is a negative regulation element (NRE; silencer binding element). Point mutations in this element enable the retroviral transcription to be improved (murine embryonic stem cell virus, MESV; M. Grez et al (1990) (22)).

The object of the invention is to provide retroviral vector hybrids which can be used to further improve retroviral gene expression especially in haematopoietic stem cells and their myeloid (non-lymphatic) derivatives.

The invention concerns retroviral vector hybrids which are characterized in that they a) contain the U5 region and/or tRNA primer binding site of MESV and/or MoMuSV in the leader region as a U5 region and/or tRNA primer binding site and b) contain the U3 and R regions from a Friend murine leukemia virus (F-MuLV) as U3 and R regions in 3'-LTR.

The vector hybrids according to the invention preferably contain the leader region of MESV as the leader region. In a further embodiment of the invention the U5 region and/or preferably the tRNA primer binding site can also be derived from MoMuSV.

The vector hybrids according to the invention also preferably contain the LTR from a Friend murine leukemia virus (F-MuLV) as the 3'-LTR and thus also the U5 region from F-MuLV in addition to the U3 and R regions from MoMuLV and MESV.

The vector hybrids can be replication-defective as well as replication-competent.

A replication-defective vector is understood as a vector which contains no retroviral gene functions (gag, env, pol) and therefore cannot independently form virus particles. However, the vector usually contains a packaging function (psi). In order to form infectious retroviral particles a packaging cell line which contains the gene functions gag, env and pol in a stable form (as an episome or integrated into the genome) is transfected with the replication-defective DNA vector according to the invention. RNA transcripts are formed which are packaged into virus particles due to the gag and env functions. These virus particles are replication-deficient because the RNA genome contained in them does not carry retroviral gene functions.

Retroviral vector hybrids capable of replication additionally contain the gene regions gag, pol and env. These gene regions can be derived from any desired retroviruses. Only the selection of the env region depends on the cell to be infected. Such methods are however, known to a person skilled in the art. In this manner it is possible to produce ecotropic, xenotropic, amphotropic or polytropic retroviruses capable of replication.

More details of this and on the production of vectors, virus particles and helper cells are described in M. Kriegler, Gene Transfer and Expression, A Laboratory Manual, W. H. Freeman & Co., New York (1990), 47–55 and 161–164 (31). This publication is a subject matter of the disclosure of the present application.

Silencer proteins within the sense of the invention are understood as cellular (e.g. derived from a mutated cell) nuclear proteins, for example from haematopoietic stem cells, which preferably bind to the first 450 bp preferably the first 18 bp, of MoMuLV and MoMuSV which immediately follow the 5'-LTR and inhibit the retroviral transcription by interaction with cis regulatory sequences of the provirus.

The leader region of MESV is understood as the sum of sequences from the short direct terminal repeat (R), the U5 region and the sequence immediately adjoining the 5'-LTR of MESV which contains the tRNA primer binding site as well as the packaging region ($\psi$). At a maximum the leader sequence can be composed of the complete sequence which is contained in the virus from R up to the translation start. However, it is preferable to use a truncated leader region which in addition to R and U5 is preferably composed of about the first 450 bases downstream of the end of the 5'-LTR region. It is also preferred that the U5 region and the tRNA primer binding site are derived exclusively or to a major extent from MESV and the other parts of the leader sequence are derived from MoMuLV or MoMuSV. A suitable MESV region is shown in the Figures (FIGS. 1–5) from KpnI (ca. 550) to BalI (ca. 729).

The leader region of MESV corresponds to the leader region of MoMuLV or MoMuSV (sequence of U3, U5 and R of MoMuLV and PCMV, see (22) and (23)) in which point mutations are inserted which reduce or prevent the binding of silencer proteins. Compared to MoMuLV and PCMV the leader region of MESV contains 5 point mutations in the 18 bp region which directly adjoins the 5'-LTR (C. Stocking et al. (1993) (21)). This drastically reduces the inhibitory binding ability of nuclear proteins from the infected cells and correspondingly improves the expression of a gene contained in the vector hybrid (R. Petersen et al., Mol. Cell Biol. 11 (1991) 1213–1221 (8)). Instead of these point mutations, other (at least one) point mutations in the leader region (preferably within the first 450 bases downstream from the end of the 5'-LTR region and particularly preferably in the 18 bp region) are also suitable for reducing or preventing the inhibitory binding of silencer proteins e.g. to the leader region. Thus in addition to the aforementioned sequence described in SEQ ID NO:1 a leader region of MESV within the sense of the invention is also understood as a sequence which essentially corresponds with this section of SEQ ID NO:1, contains a tRNA binding site and a psi function and is modified by point mutations in such a way that the inhibitory binding of silencer proteins from the cells which have been chosen for the transfection is reduced or prevented.

In order to check whether a point mutation is suitable for preventing the binding of silencer proteins to the leader region it is usual to construct a plasmid which contains an LTR, the leader region to be examined and an indicator gene which is preferably the CAT gene. The cells to be examined are transfected with this plasmid and the CAT activity is determined preferably after 48 hours (transient transfection). If the CAT activity is clearly present then the point mutation is suitable for preventing the binding of the silencer protein in these cells (P. Artelt et al. (1991) (32)).

Transient transfection experiments have shown that cis-regulatory sequences are located in the leader sequence of MoMuSV that have an inhibitory influence on the gene expression in particular in early multipotent myeloid cells (primary silencing). A substitution of this region by leader sequences of the murine embryonic stem cell virus [MESV (22)] completely abolishes the inhibitory effect in myeloid stem cells. The leader sequence of MESV was originally derived from the endogenous mouse retrovirus dl-587rev (23) and was introduced into MESV in order to abolish the silencing of the MoMuSV leader observed in embryonic stem cells (22). Mutations of the retroviral primer binding site (PBS) which is located immediately 3' of the 5'-LTR are decisive for the abolition of the silencing (22).

Retroviruses of the F-MuLV group are known to a person skilled in the art and are described for example in D. Linnemeyer et al. (1981) (7), J. Friel et al. (1990) (9), S. P. Clark and T. W. Mak (1982) (10), L. Wolff et al. (1985) (11), R. K. Bestwick et al. (1984) (12), W. Koch et al. (1984) (13) and A. Adachi et al. (1984) (14). A review is given in W. Ostertag et al. (1987) (15). The 3'-LTRs of malignant histiosarcoma virus (MHSV) (9), SFFVp Lilly-Steeves (10), SFFVa (11), Rauscher SFFV (12), F-MuLV c157 (13) and Friend-mink cell focus forming virus (F-MCFV FrNx (14), F-MCFV pFM548 (13)) are preferably used.

According to the invention sequences of the genomic vector RNA are suitable as 3'-LTR sequences which have a high degree of sequence homology to the 3'-LTR regions of the aforementioned Friend virus family in the U3 region. The LTR sequence of SFFVp is described in SEQ ID NO:1 (nucleotides 1707–2283).

The advantages according to the invention are exhibited in transient transfections of reporter gene constructs in numerous representative cell lines of humans and mice. It has surprisingly turned out that U3 sequences of mouse retroviruses of the Friend murine leukemia virus (F-MuLV) family in combination with leader sequences (preferably tRNA binding site) of MESV enable an especially efficient gene expression in myeloid stem and precursor cells. The increase of the gene expression with the vector hybrids according to the invention is more than a power of ten compared to MoMUSV. This applies to relatively late precursor cells of the granulocytes, macrophages and erythrocytes as well as to the early multipotent precursors and even stem cells of the myeloid system. The vector hybrids according to the invention enable an efficient gene expression especially in the case of immature multipotent myeloid cells in which MoMuSV-LTR exhibits a pronounced primary silencing. The activity is also high in the lymphatic system as well as in fibroblasts.

An early isolate of the polycythaemia-inducing spleen focus forming virus (SFFVp (7)), is particularly preferred whose LTR sequence is described in SEQ ID NO:1 (bp 2654–3230) as well as the malignant histiosarcoma virus (MHSV (9), LTR SEQ ID NO:4, bp 1707–2324). In the U3 region of these viruses there is a high degree of sequence homology to other representatives of the Friend virus family such as SFFVp Lilly-Steeves (10), SFFVa (11), Rauscher SFFV (12), F-MuLV c 57 (13) and Friend-mink cell focus forming virus [F-MCFV FrNx (14), F-MCFV pFM548 (13)]. These and similar Friend-related retroviruses have a similar expression pattern as SFFVp and MHSV due to the sequence homology of the U3 regions.

Mutations in the enhancer region of U3 [340 to 140 nucleotides on the 5' side of the transcription start (10)] are particularly advantageous for the pronounced increase compared to MoMuSV of the gene expression in myeloid stem and precursor cells by the vectors according to the invention. The partial duplication of the so-called direct repeat element in SFFVp (similar to F-MCFV FrNx) and MHSV is of importance. Binding sites for transcription factors may be located here which lead to an efficient gene expression in myeloid cells.

SFFVp and MHSV as well as Friend MCFV carry a binding site for the transcription factor Sp1 (16) directly 5' of the direct repeats. Sp1 is capable of multiple interactions with surrounding transcription factors which usually lead to a considerable increase in gene expression. In the case of the MoMuSV derivatives myeloproliferative sarcoma virus (MPSV (17), (18)) and PCC4-cell passaged MPSV (PCMV (19)) the occurrence of an Sp1 binding site in the U3 region is also necessary for the abolition of the silencing of the MoMuSV-LTR in embryonic stem cells (20) as well as probably also in blood stem cells (21). The Sp1 binding site of SFFVp, MHSV as well as Friend-MCF viruses may also have an analogous function.

In a further embodiment of the invention the retroviral vector hybrids can contain the U3 and R regions from MPSV as U3 and R regions in 3'-LTR. MPSV differs from MoMuSV and MoMuLV by point mutations in the LTR (21). In this case A(−381) is deleted and the following substitutions have been carried out C→T, −345; T→A, −326; T→A; −249 and A→C, −166 (numbering according to (21)). In this case the retroviral vector hybrid contains the U5 region and tRNA primer binding site of MESV in the leader region as the U5 region and tRNA primer binding site. It has turned out that such MPSV/MESV hybrid vectors (also called MPEV in the following) have considerable advantages compared to vectors based on MoMuLV and are of major importance for numerous applications in somatic gene therapy.

Any desired U3 and R regions can be used in 5'-LTR since after integration of the virus the U3 from the 3'-LTR is copied in the target cell also at the 5'-LTR position after completion of the retroviral life cycle and drives the gene expression. U3 and R regions are derived for example from MoMuLV or MoMuSV derivatives such as for example MPSV, PCMV and MESV. 5'-LTRs from F-MuLV are also suitable as the 5'-LTR.

The vector hybrids according to the invention exhibit a high tissue-specific expression after retroviral transduction of myeloid stem and precursor cells. These vectors therefore have the potential to considerably increase the gene transfer efficiency in myeloid stem and precursor cells compared to MoMuSV vectors. The vectors according to the invention additionally have the potential to be considerably less subject to silencing processes in myeloid cells than MoMuSV vectors. The high and possibly even persistent gene expression of these vectors in myeloid cells can form the basis for the successful application of numerous gene transfer protocols on the blood-forming system of humans. The constructs described in the examples are constructed in such a way that the cDNAs transferred by the vector can be replaced without difficulty by other genes.

The tissue specificity of the expression is suitable for abolishing the primary silencing in the myeloid system observed in the case of conventional MoMuSV vectors. This leads to a considerable increase in the functional gene transfer rates in myeloid cells. Since a high functional gene transfer rate is desired in most gene transfer/gene therapy applications on the myeloid system this is a generally usable advantage of the constructs according to the invention.

The Friend virus-related U3 regions were also selected in the myeloid system of the mouse for persistency of the gene expression in vivo. Secondary silencing occurred with these vectors to a much lower extent than with MoMuSV vectors. The exclusion of inhibitory leader sequences by substitution for MESV sequences is of additional advantage in this regard. This is of importance for all gene transfer/gene therapy applications in which a persistent (if possible life long) expression of the retrovirally transferred sequences is desired in the myeloid system (gene marker studies, correction of metabolic defects).

For this purpose the vector hybrids according to the invention can contain at least one gene that is heterologous for the virus and can be expressed in eukaryotic cells. Such genes are for example the multiple drug resistance gene (MDR gene), an antibiotic resistance gene such as the neo$^R$ gene, the LNGFR gene, the cerebrosidase gene or the herpes simplex TK gene. In a preferred embodiment several and preferably two or three heterologous genes can also be contained in the vector hybrid. In order to enable an expression of these separate genes, it is expedient to insert a promoter, a splicing site (preferably from SF7Vp) or an internal ribosomal entry site (IRES preferably from polio viruses (I. R. Ghattas et al. (1991) (26)) in front of the second or third gene.

The production of a high virus titre in fibroblastoid packaging cell lines is a further important requirement for retroviral vectors which are intended to be used for gene transfer in myeloid cells. In the case of all the construct examples listed below the activity of the Friend-related U3 regions in fibroblastic retrovirus packaging cell lines is adequate to produce the required titre of $10^5$ to $10^6$ vector-transferring retroviral particles/ml cell culture supernatant.

Accordingly a subject matter of the invention is also a process for the production of a retrovirally transduced eukaryotic cell which contains an active exogenous gene which is characterized in that the eukaryotic cell is transduced with a replication-defective retroviral vector virus which in its genome contains a) the leader region of MESV or MoMuSV as the leader region
b) the U3 and R regions from a Friend murine leukemia virus (F-MuLV) as the U3 and R regions in the 3'-LTR and
c) the said exogenous gene.

The LTR from F-MuLV is preferably used as the 3'-LTR which then contains the said U3 and R regions.

A further subject matter of the invention are retrovirally transduced, eukaryotic cells obtainable by transducing the eukaryotic cell with a replication defective retroviral vector virus which in its genome contains a) the leader region of MESV and/or MoMuSV as the leader region
b) the U3 and R regions from a Friend murine leukemia virus (F-MuLV) as the U3 and R regions in the 3'-LTR.

This vector optionally contains one or several (up to three) exogenous genes which can be expressed in the eukaryotic cell. Mammalian cells preferably haematopoietic cells and especially haematopoietic stem cells are preferably used as eukaryotic cells. The LTR from F-MuLV is preferably used as the 3'-LTR which then contains the said U3 and R regions.

An active exogenous gene is understood as a gene which is introduced from outside into the cell and is expressed (is active) in this cell after integration into the genome. The exogenous gene may be a gene not present in the cell genome (e.g. an antibiotic resistance gene such as neo$^R$, LNGFR receptor (D. Johnson et al. (1986) (33)), the cerebrosidase gene or a herpes simplex TK gene) or a gene present in the genome but not expressed there or only to an inadequate extent such as the multiple drug resistance (MDR) gene.

A further subject matter of the invention is a replication-defective infectious virus particle which contains a retroviral RNA as the genome wherein the genome contains a leader region from MESV which contains a packaging function and a tRNA binding site, and contains a heterologous gene for the virus which can be expressed in a eukaryotic cell and contains at the 3' end U3 and R from a Friend murine leukemia virus (F-MuLV) but no active gag, env and pol sequences.

A further subject matter of the invention is a process for the production of a replication-defective infectious virus particle by transfection of a eukaryotic helper cell which possesses the helper functions gag, env and pol with a vector hybrid which contains the leader region of MESV as the leader region and the LTR from a Friend murine leukemia virus as the 3'-LTR, production of the RNA corresponding to the DNA of the vector hybrid as a virus genome in the cell (for example by cellular polymerases), packaging of the said RNA into the replication-deficient empty virus envelopes that are formed in the cell and isolation of the infectious virus particles which contain the said virus genome.

A further subject matter of the invention is the use of a replication-defective retroviral vector hybrid according to the invention which contains the leader region of MESV as the leader region and the U3 and R regions from a Friend murine leukemia virus (F-MuLV) as the U3 and R regions in the 3'-LTR for the production of a pharmaceutical agent for ex vivo or in vivo gene therapy.

Vector hybrids are also suitable for the process and uses according to the invention which contain the U5 region and/or tRNA binding site of MESV or MoMuLV/MoMuSV in the leader region as the U5 region and/or tRNA binding site.

Areas of Application

I. All somatic gene transfer/gene therapy methods in which myeloid stem cells and precursor cells are the target population for retroviral vectors.

In the individual protocols different cDNAs are integrated into the vectors. Examples are Gene marker studies (1): Selectable marker genes such as neoR or shortened nerve growth factor receptor are transferred in order to monitor the fate of the labelled cell population in the organism under the conditions of the examined disease/therapy. The neoR vectors pSF1N and pMH1N which carry the neoR under the control of the SFFVp U3 and MHSV U3 (MESV leader) exhibit in comparison to neoR-transferring Maloney vectors a considerable increase in the functional gene transfer rate in the model system of the mouse stem cell line FDCPmix. They are suitable for neoR transfer in human myeloid stem cells.

Protection of bone marrow against the side-effects of a high dose chemotherapy (28): genes mediating chemotherapy resistance such as MDR1 or alkyl transferases are transferred. High transfer rates and expression via the optimized Friend virus-related vectors prevent myelosuppressive side-effects and eventually also secondary tumour induction of the chemotherapy.

Correction of metabolic diseases: In the case of monogenic hereditary diseases intact copies of the defective genes are introduced by means of retroviral gene transfer into myeloid stem cells. Applications are for example conceivable in the case of hereditary diseases whose gene defect has effects on the myeloid system (storage diseases such as the Hurler syndrome; M. Gaucher (29)):

II Cloning of replication-competent Friend-related retroviruses

Due to their extended host spectrum towards early myeloid stem and precursor cells the viruses according to the invention are particularly well suited for insertion mutagenesis in these cells. Insertion mutagenesis enables genes to be cloned which have an important function in the physiological growth regulation of the myeloid system.

The principle of using retroviruses as an insertion mutagen has already been described several times (Review: Kung et al. (1991) (34)). Retroviruses integrate DNA sequences unspecifically into the genome and in this process can activate or inactivate genes. Replicatable retroviruses infect tissues with a very high efficiency and can therefore increase the probability of producing mutations by integration. Such mutations can in turn lead to a degeneration of the mutated cells i.e. tumours are formed.

In in vivo experiments with mice (usually on new-born mice since they do not yet have an immune system which works efficiently and are therefore very sensitive towards retroviruses) for the identification of regulatory genes, these are infected with retroviruses and, after a latency period of about 3 months, it is possible to discover and examine specific tumours (dependent on the virus type). Analyses of the clonal retroviral integration sites reveal genes whose activation or inactivation can lead to cells of a modified or degenerate phenotype. This enables a large number of diverse gene types to be discovered such as genes for ligands, receptors, signal transducers and transcription factors. It is significant that there is a high correlation between the tumour type found which is produced by particular viruses and the activated/inactivated gene (e.g. in the case of erythroleukemia which is induced by Friend-MuLV ca. 80% of the tumours exhibit integration events in the Fli-1 locus and transcriptional activation of the transcription factor PU-1 gene: It was possible to identify interacting oncogenes by infecting transgenic mice with ecotropic expression of an oncogene (e.g. myc) and observing the tumorigenesis. After a considerably shortened latency period tumours were formed by secondary mutations ("second hit" e.g. in the pim-1 gene)). Nevertheless it has only been possible to identify some of the possible genes using the previous retrovirus constructs. The spectrum of genes that can be identified with this approach of activation/inactivation and the concomitant phenotypic modification of the cell depends strongly on the specificity of the retroviruses used for particular cell types. Thus retroviruses that have been previously used only exhibit a very low infectiousness in haematopoietic and embryonic stem cells (cf. Review: Stocking et al. (1993) (21)). This is due to several reasons; primarily to transcription control elements in the retroviral LTRs (Stocking et al. (1985) (18)) and secondarily also due to the protein interactions between cellular and viral proteins that are necessary for viral replication.

Replication-competent retroviruses produce new cells producing retroviruses by infection which leads to a complete infection of the entire cell population and to a much higher probability of forming mutations. A similar efficiency can only be achieved by a much more complicated and time-consuming co-cultivation of the retrovirus packaging line with the target cell line.

Friend-related replication-competent viruses can in addition be used to produce forced passage mutants which also have an additional improvement of the infectiousness towards blood stem cells. Mutations in retroviral structural proteins of these viruses may be used to produce optimized packaging cell lines for gene transfer into myeloid cells. Mutations in cis regulatory sequences of these viruses may be used to further optimize retroviral vectors for blood stem cell gene transfer.

A further subject matter of the invention are ecotropic, xenotropic, amphotropic or polytropic retroviruses capable of replication containing the regulatory elements (leader region) of MESV and optionally MoMuLV or MoMuSV combined with the U3 and R regions from a Friend murine leukemia virus (F-MuLV) as U3 and R regions in the 3'-LTR, which as a result are capable of more efficiently infecting murine (in vivo and in vitro) or human (in vitro) precursor cells and to trigger mutations. The retroviruses preferably contain the LTR from F-MuLV as the 3'-LTR.

The combination of both components leads to retroviral insertion mutagenesis constructs of a new quality which can be used to identify genes which cannot be detected with conventional replicatable retroviruses. They can be produced in a very high titre and result in an almost 100% infection rate since each infected cell becomes a production cell for new viruses. The neomycin resistance gene which is used in retroviral vectors for selection can be deleted in them. This leads to a higher transcription of the LTR promoters since $neo^R$ functions as a silencer (Artelt et al. (1991) (32)) and consequently leads to an improved insertion rate.

Murine as well as human haematopoietic and embryonic stem cells can be infected in vitro with a high efficiency by the retroviruses according to the invention and mutants can be produced by insertion into the genome (activation or inactivation of genes). Therefore also in the case of in vivo experiments it would be expected that the viruses according to the invention would infect early haematopoietic and embryonic cells with a higher efficiency and to activate or inactivate genes by integration into the genome.

Gene activation can occur in several ways. Thus integration upstream of a gene can activate it under the transcriptional control of the 3'-LTR promoter. The binding sites of negative control elements can also be inactivated which can lead to a gene activation. There are also several examples (Kung et al. (1991) (34)) which demonstrate that the 5'-LTR promoter can activate a gene after insertion is completed either directly by reading through or by its enhancer effect many bases upstream of and also within an intron.

An integration within a gene or in the accompanying promoter/enhancer region can also lead to an inactivation of the corresponding gene.

If genes are effected which are important for the regulation of the cell it is possible that the cells degenerate i.e. tumours may be formed. The viruses according to the invention can therefore be used to find other genes e.g. genes which are involved in the cell regulation of haematopoietic or embryonic stem cells which are different from those that can be found by conventional viruses which do not replicate or only very poorly in such cell types.

The replication-competent viruses according to the invention can also be used in vitro for example in the following manner:

Factor-dependent promyelocytic cell lines were made factor-independent by retroviral insertion mutagenesis i.e. the growth factor gene was activated by retroviral integration. The retrovirus infection was achieved by co-culturing the target cell line with packaging lines producing the MPSV vector. This in vitro approach can be made more efficient by using the constructs according to the invention. Moreover murine or human embryonic and haematopoietic stem cells can also be used in the above investigations using the viruses according to the invention.

A further application is in experiments which have the goal of producing improved vector virus packaging lines, e.g. for gene therapy, which can produce viruses with a higher infection efficiency in precursor cells. In these cells there are several blocks which interfere with the retroviral infection/replication. The use of the constructs according to the invention has the advantage over replicatable wild-type MoMuLV or AM4070 that the transcriptional blocks are already removed. Improvements in the infection efficiency can therefore be attributed to corresponding mutations in the viral proteins.

A further application of the constructs according to the invention is to produce "knock out" mice by insertion inactivation of one or several genes in embryonic stem cells.

The invention is further elucidated by the following examples, diagrams and sequence protocols.

The sequence protocols show:

SEQ ID NO:1 sequence of pSF1
SEQ ID NO:2 sequence of pSF2
SEQ ID NO:3 sequence of pSF3
SEQ ID NO:4 sequence of pMH1
SEQ ID NO:5 sequence of pSF-MDR
SEQ ID NO:6 sequence of pMP-MDR (only the proviral part of the sequences is shown in each case)

EXAMPLE 1 a) Description of construction

Table 1 shows the cloning strategies of the constructs according to the invention.

Figure 1A:
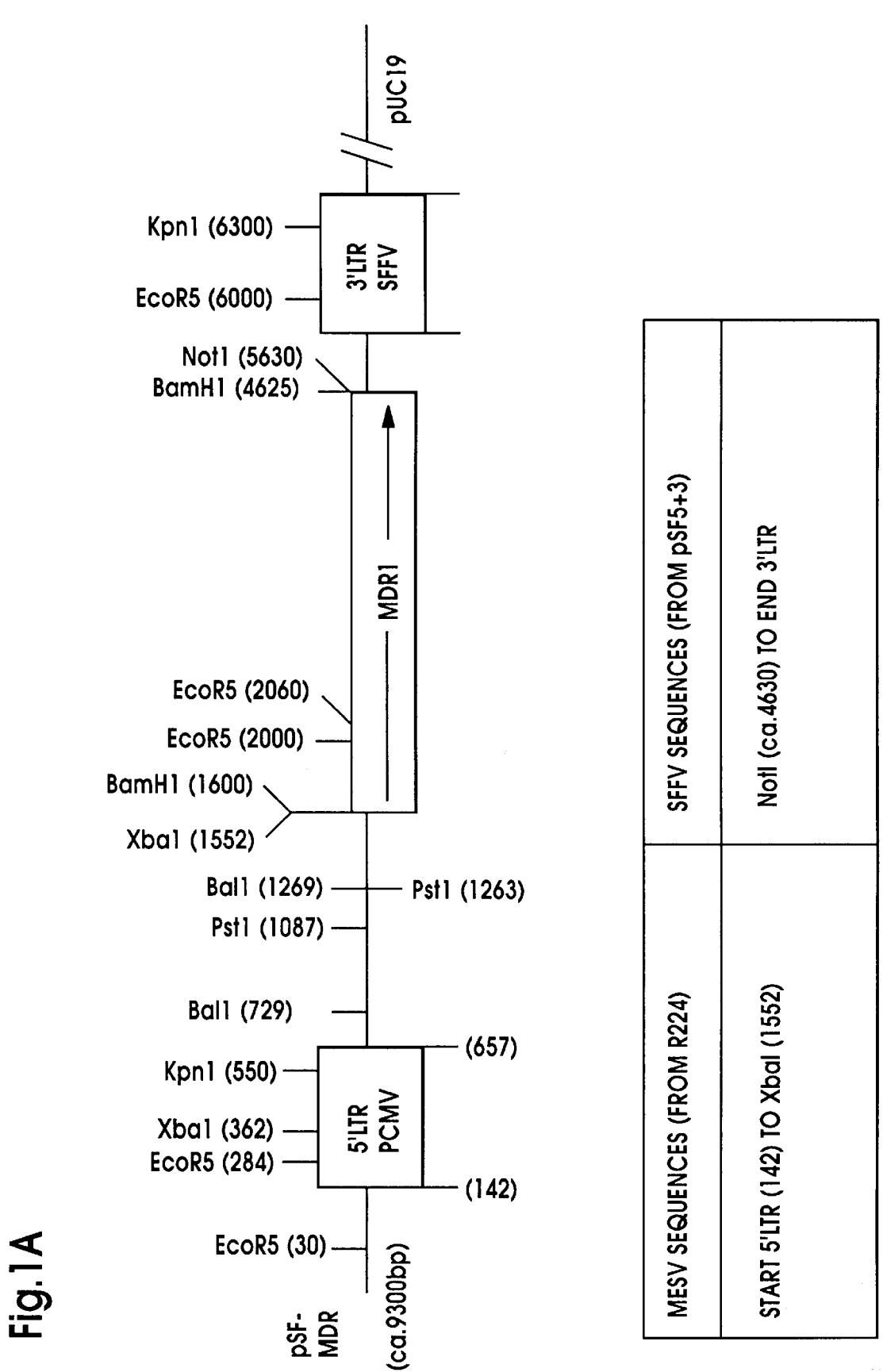
FIG. 1A shows the plasmid map of pSF-MDR: (information on restriction sites for guidance)
Figure 1B:
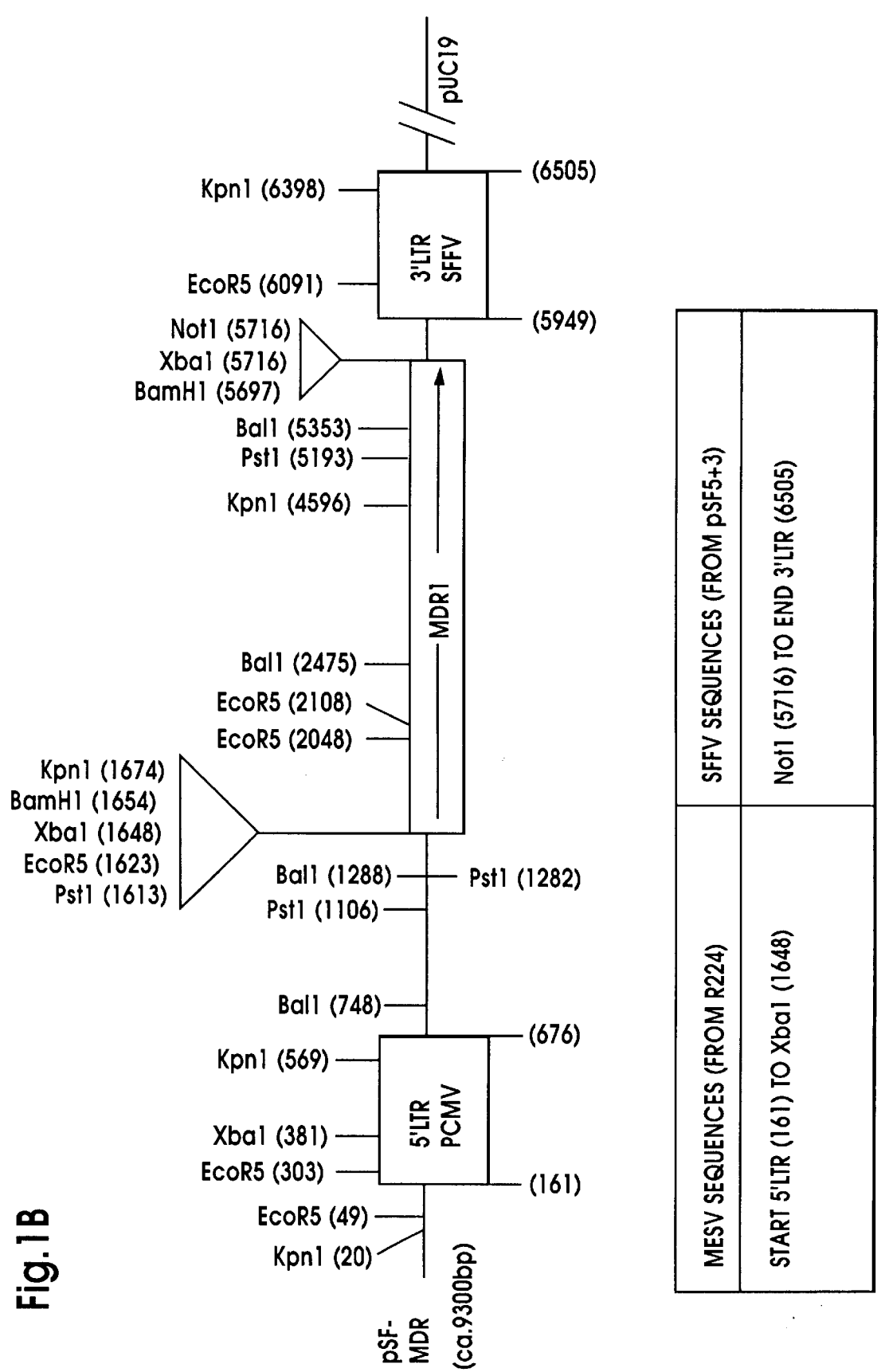
FIG. 1B shows the plasmid map of pSF-MDR (more exact details of restriction sites)
Figure 6:
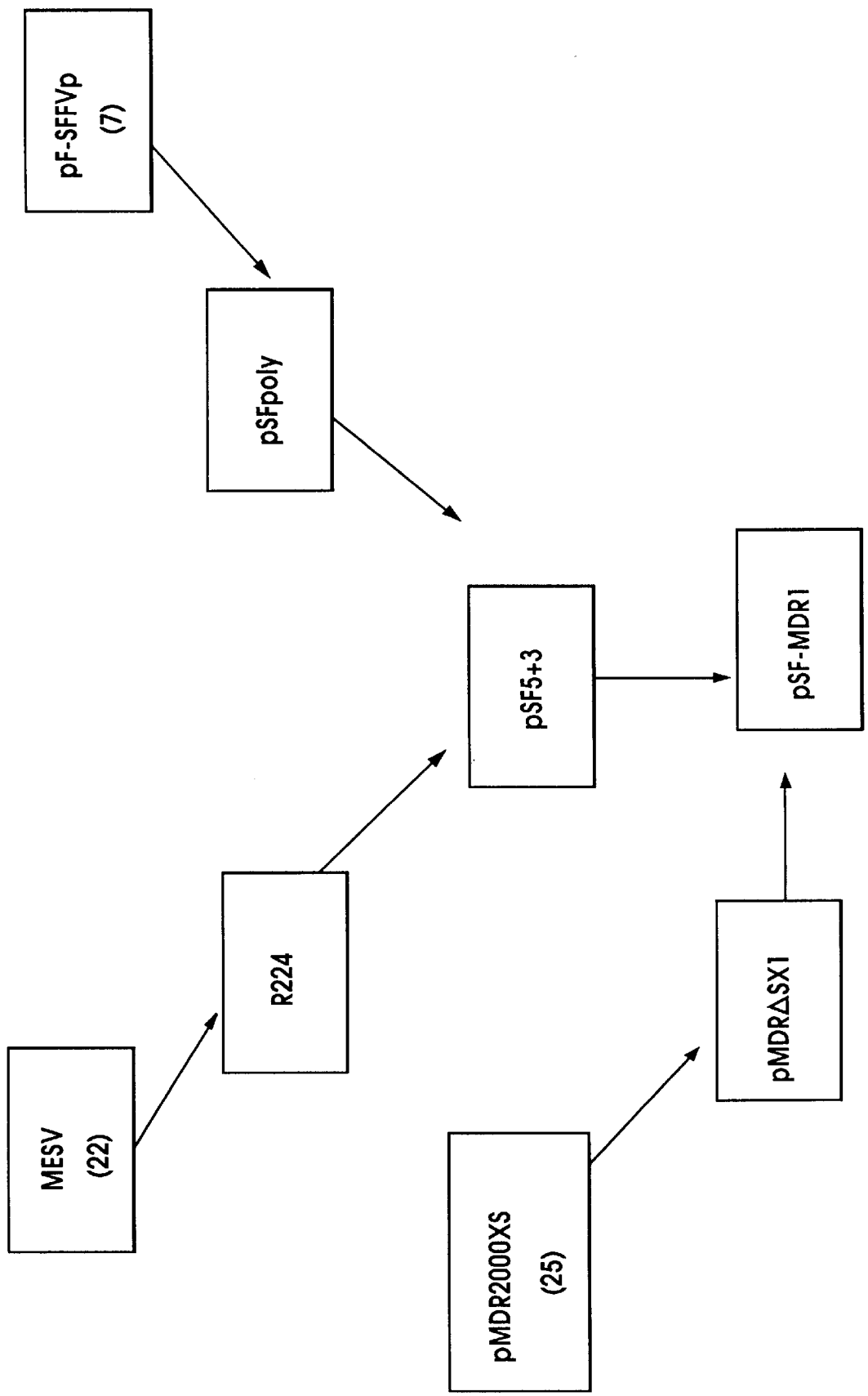
FIG. 6 shows the scheme for the formation of vector pSF-MDR1.
Figure 7:
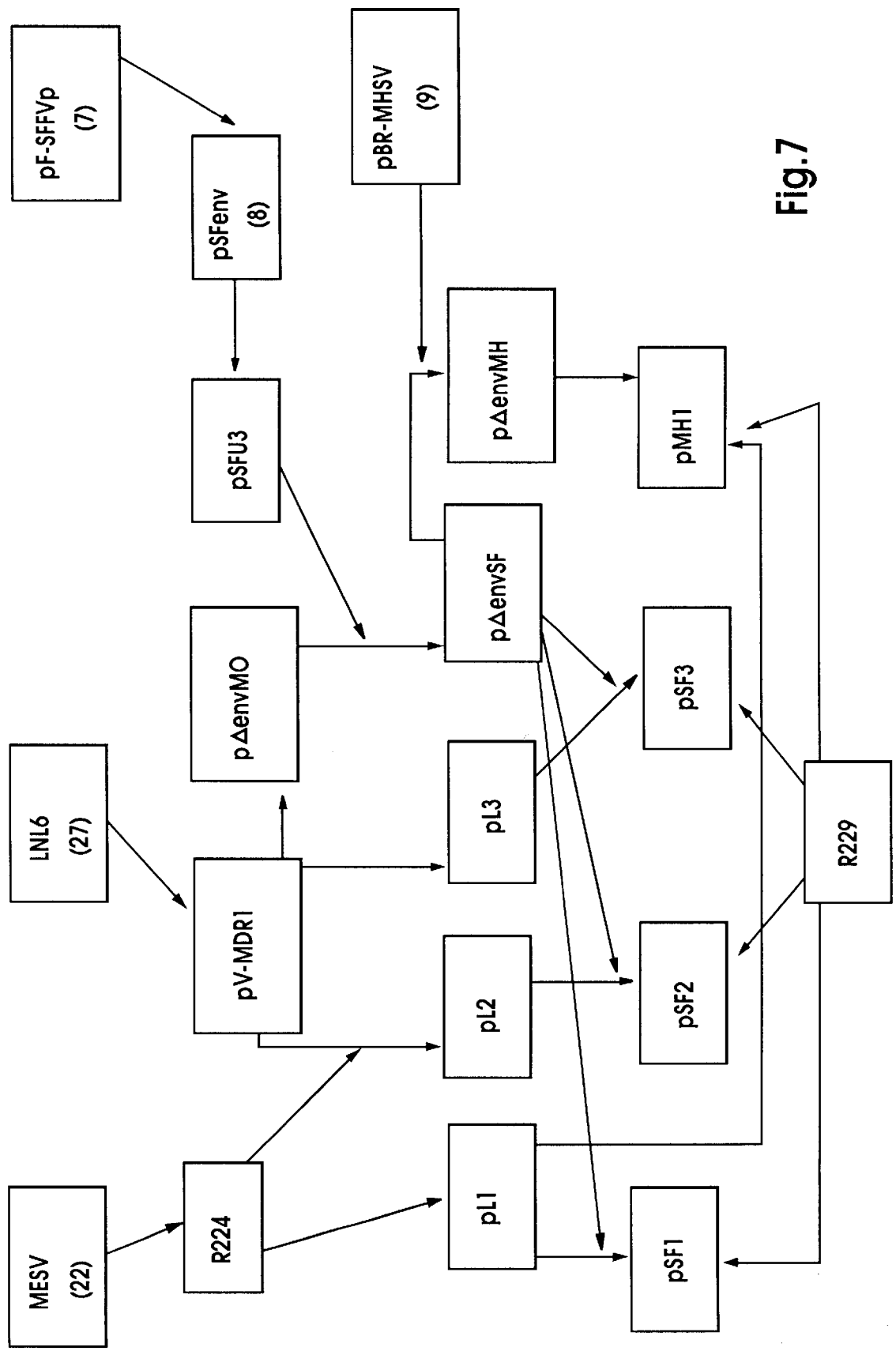
FIG. 7 shows the scheme for the formation of vectors pSF1N, pSF2N, pSF3N and pMh1N.
Figure 8A:
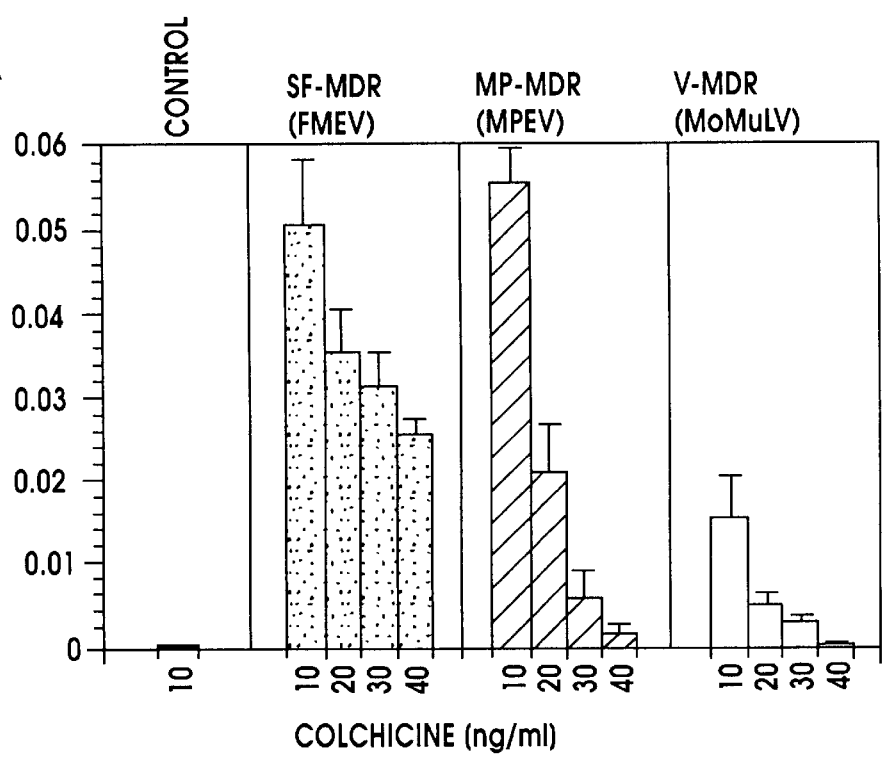
FIG. 8 shows the protection of myeloid cells by FMEV and MPEV-mdr1 vectors in comparison to standard MoMuLV vectors. The average relative transduction frequency is stated (corrected for fibroblast titres and cloning efficiency). Fibroblast titres between the various vectors vary by less than factor 3. A: cell line K-562, B: cell line TF-1.
Figure 8B:
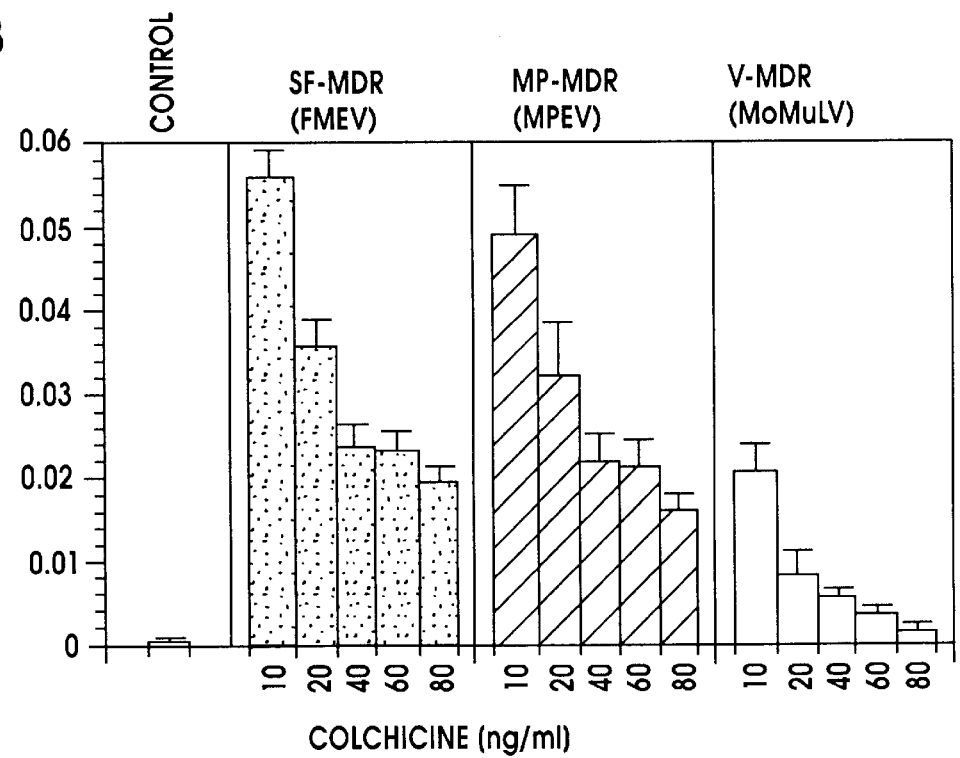

I. pSF-MDR (FIGS. 1, 6, Table 1, SEQ ID NO:5)

This vector was cloned based on the MESV vector R224 (base pUC 19) in which parts of the env region as well as the complete U3 region of the 3'LTR were replaced by SFFV-p sequences. Vector pSF5+3 (cf. FIG. 6) was obtained in this manner. In a second step the cDNA (from pMDR2000XS (25)) coding for MDR1 was inserted into the multiple cloning site (NotI, XbaI, BamHI, Hind3).

II. pSF1N, pSF2N, pSF3N, pMH1N (FIGS. 2–5, 7, Table 1)

The backbone of these plasmids is based on the MESV vector R224 in which a major deletion had been carried out between the Xba1 cleavage site of the the 5'LTR and the Kpn1 cleavage site in the 3'LTR. The complementing sequences were inserted by means of three fragment ligations; base vectors pSF1, pSF2, pSF3 and pMH1 result (formation scheme and cloning strategy, FIG. 7, Table 1, sequences described in SEQ ID NO:1–4). The fragments used for the three fragment ligation are obtained from auxiliary constructs (see formation scheme, FIG. 6) in which simple modifications can be carried out in order to further optimize the vectors. It is also conceivable to substitute the SFFVp or MHSV U3 regions by analogous sequences of other Friend-related retroviruses or by the above-mentioned modifications of the leader in order to optimize the titre. The construct examples pSF 1N, pSF2N, pSF3N, pMh1N were obtained after insertion of the neoR cDNA (from R229). The construct examples carry polylinkers with singular restriction cleavage sites which can be used for the exchange of genes to be transferred. At these cleavage sites it is additionally possible to insert regulatory sequences for secondary gene expression that may be necessary such as the splice acceptor of SFFVp or the so-called internal ribosome entry site IRES (I. R. Ghattas et al. (1991) (26)).

The Friend-related regions cloned in the construct examples as U3 and R (in the 3'-LTR) are also copied at the 5'-LTR position after completion of a retroviral life cycle and then drive gene expression in the target cells. The construct examples contain all cis regulatory elements necessary for retroviral gene transfer and retroviral gene expression. Properties of SFFVp (or MHSV), MESV and MoMuSV are combined in these constructs. The point mutation of the start codon for the retroviral gag protein to form a stop codon (A. D. Miller and G. J. Rosman (1990) (27)) and the deletion of superfluous env sequences (27) are integrated as safety-relevant modifications in pSF1N, pSF2N, pSF3N, pMH1N.

gene expression rate in transduced cells. This is important in gene transfer applications whose success also depends on the level of gene expression (see example of application: protection of bone marrow in high-dose chemotherapy). If the cells are plated out with very high doses of cytostatic agents (ca. 20-fold LD50 for TF1) in the experiment described above (infection of human myeloid cells with SFMDR or V-MDR) only cells infected with SF-MDR are able to form colonies (Table 2).

TABLE 1

Cloning strategies for the constructs and auxiliary constructs according to the invention.

| Construct | Backbone | Fragment 1 | Fragment 2 |
|---|---|---|---|
| pSFMDR | SF5 + 3 Sal1/not1 | pMDRSX1 Sal1/Not1 | |
| pSF5 + 3 | R224ΔNB Xho 1/Nru1 | psFpolyHind3 blunt end | |
| pMDRΔSX1 | bluescript KS Sal1/Sma1 | pMDR2000XS Sal1/Ssp1 | |
| pSF1N | pSF1 Not1/BamH1 | neoR Not1/BamHI (R229) | |
| pSF2N | pSF2 Not1/BamH1 | neoR Not1/BamHI (R229) | |
| pSF3N | pSF3 Not1/BamH1 | neoR Not1/BamHI (R229) | |
| pMH1N | pMH1 Not1/BamH1 | neoR Not1/BamHI (R229) | |
| pSF1 | R229ΔXba1/Kpn1 | pLl Xba1/Not1 | pΔenvSF Not1/Kpn1 |
| pSF2 | R229ΔXba1/Kpn1 | pL2 Xba1/Not1 | pΔenvSF Not1/Kpn1 |
| pSF3 | R229ΔXba1/Kpn1 | pL3 Xba1/Not1 | pΔenvSF Not1/Kpn1 |
| pMH1 | R229ΔXba1/Kpn1 | pLl Xba1/Not1 | pΔenvMH Not1/Kpn1 |
| pL1 | bluescript KS Xba1/Not1 | R224 Xba1/Not 1 | |
| pL2 | pL1ΔBal1 | pV-MDR 1 Bal1 | |
| pL3 | pL1ΔKpn1-Pst1 | pV-MDR1 Kpn1/Pst1 | |
| pΔenvMO | bluescript KSBamH1/Kpn1 | pV-MDR1 BamH1/Kpn1 | |
| pΔenvSF | pΔenvMo Nhe1/Kpn1 | pSFU3 Xba1/Kpn1 | |
| pΔenvMH | pΔenvSF EcoR5/Kpn1 | pBR-MHSV EcoR5/Kpn1 | |
| pSFU3 | pUC19 Hinc2 | pSFenv SfaN1/Kpn1 | |

EXAMPLE 2

Increasing the functional gene transfer rate in comparison to conventional Moloney vectors The multiple drug resistance 1 (MDR1) gene codes for an efflux pump located in the membrane (P-glycoprotein) which mediates resistance to a series of clinically important cytostatic agents (I. Pastan et al. (1988) (25)). The degree of resistance is closely related to the level of expression of P-glycoprotein. If myeloic stem cells are successfully made resistant to cytostatic agents by retroviral MDR1 transfer, this could make an important contribution to lowering the side-effect rate in tumour chemotherapy.

In the experiment K562 cells (ATCC CLL243) and TF-1 cells (human myeloid progenitor cell lines) were infected with retroviral vectors which express MDR1 under the control of the SFFV-LTR (virus SF-MDR resulting from the construct pSF-MDR with MESV leader and MPSV/MESV hybrid vector pMP-MDR).

The TF1 cell line was obtained from a patient with erythroleukemia as described by T. Kitamura et al. (1989) (30). The cells are kept in culture in RPMI medium (supplemented with 20% foetal calf serum, 1 mM Na pyruvate, 4 mM glutamine and 20 U/ml recombinant GM-CSF).

K562 cells and TF1 cells were infected in an identical mixture with a Moloney-MDR1 vector (virus V-MDR resulting from the construct pVMDR) which is used in a clinical gene transfer protocol under the leadership of Prof. A. Deisseroth at the MD Anderson Cancer Center, Houston, Tex. As can be seen from Table 2 SF-MDR in the case of K562 leads to a 20-fold increase of the gene transfer rate compared to VMDR as measured by the number of colonies growing when cytostatic agents are administered (ca. 10-fold LD50 for K562).

The increase of the functional gene transfer rate in myeloid cells is an expression of the average increase of the

TABLE 2

Colony number under colchicine selection after infection of human haematopoietic cells K562 and TF1 by MDR1-transduced retroviral vectors. The vectors pSF, MDR and pMP-MDR considerably increase the functional gene transfer rate compared to a conventional MoMuLV vector.

| | | | Number of colonies under selection | |
|---|---|---|---|---|
| Virus | U3 region of 3'LTR | Leader | K562 (20 ng colchicine) | TF1 (80 ng cochicine) |
| SF-MDR | SFFVp | MESV | 948 +/− 98 | 13 +/− 3 |
| V-MDR | MoMuLV | MoMuSV | 38 +/− 4 | 0 |
| MP-MDR | MPSV | MESV | 410 ± 28 | 9 ± 3 |

The cells were infected with a retroviral supernatant of amphotropic packaging cell lines. The titre of fibroblasts was ca. $2 \times 10^4$/ml for both vectors at the time of the experiment. The ratio of vector/target cell was <1 during infection. 24 hours after the infection $5 \times 10^4$ cells were plated out in soft agar medium containing colchicine. The evaluation was carried out on day 8 of the agar cloning. The cloning efficiency without selection was ca. 15% for both cell lines. The experiments were carried out in duplicate.

Analogous results are obtained to those of vector pV-MDR for a vector whose U3 region is derived from MoMuLV and whose leader is derived from MESV.

In the MDR1 system constructs with an MESV leader have slightly reduced titres compared to conventional MoMuSV vectors. This may be due to mutations in the packaging region of MESV. Hybrids between the leader sequences of MESV and MoMuSV have the potential to produce vectors with a higher titre due to an improved packaging function in retroviral packaging cell lines with simultaneous exclusion of cis-inhibitory sequences. This was taken into account when cloning the construct examples pSF2N and pSF3N.

Note: Proviral vectors are for example denoted SF-MDR, MP-MDR etc. in order to differentiate them from the corresponding plasmids pSF-MDR, pMP-MDR etc.

EXAMPLE 3

Figure 2A:
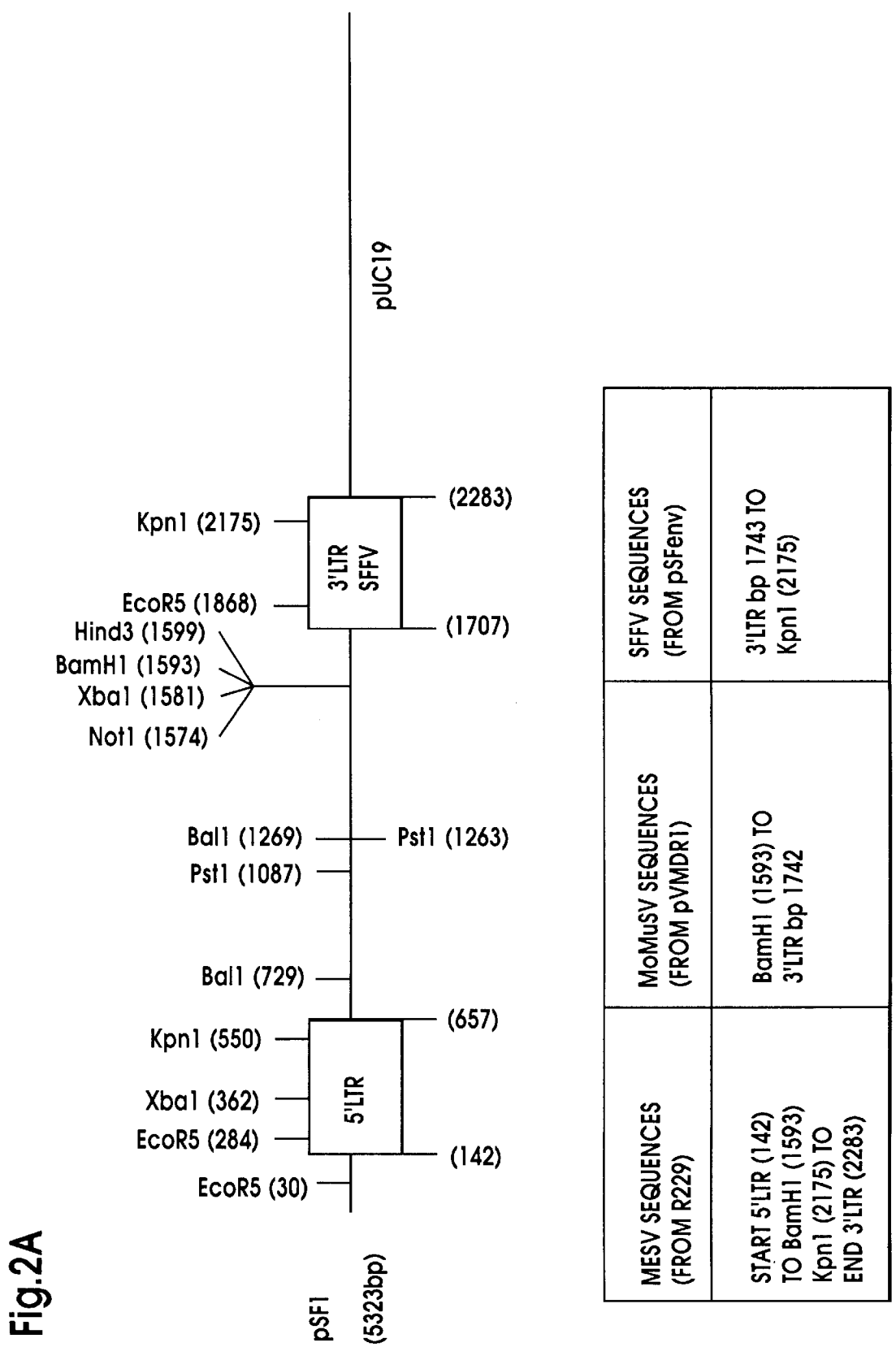
FIG. 2A shows the restriction map of pSF1
Figure 2B:
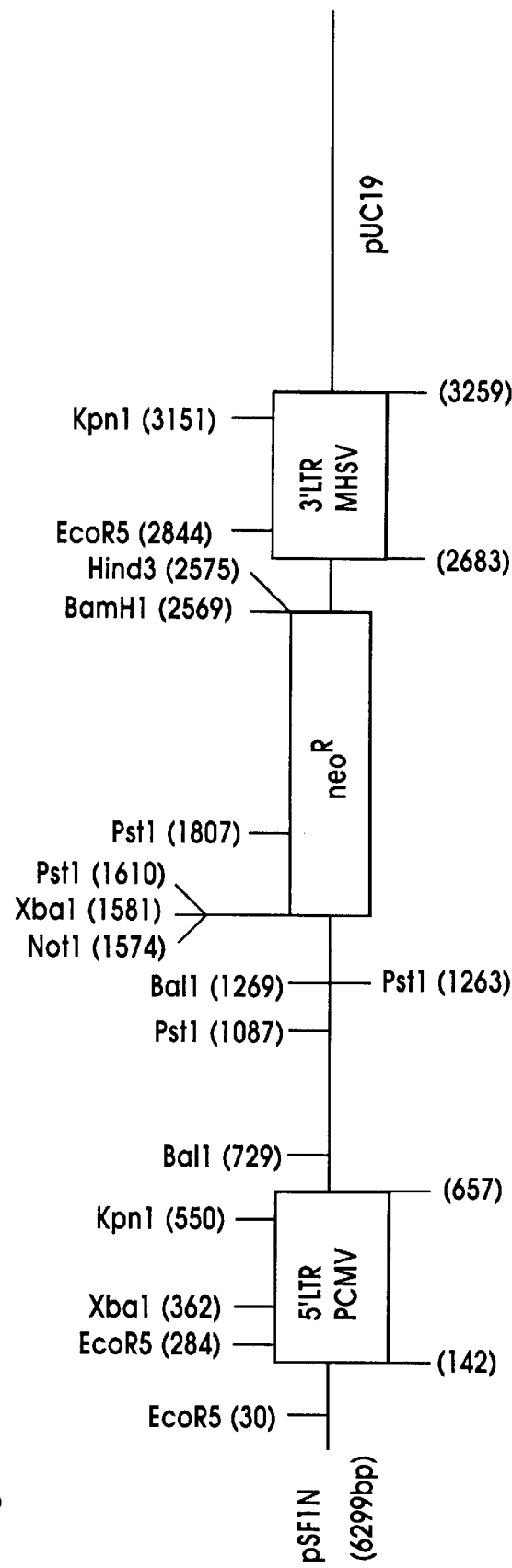
FIG. 2B shows the restriction map of pSF1N. This vector corresponds to pSF1 into which the neo$^R$ gene was inserted into the multiple cloning site (MCS).
Figure 3A:
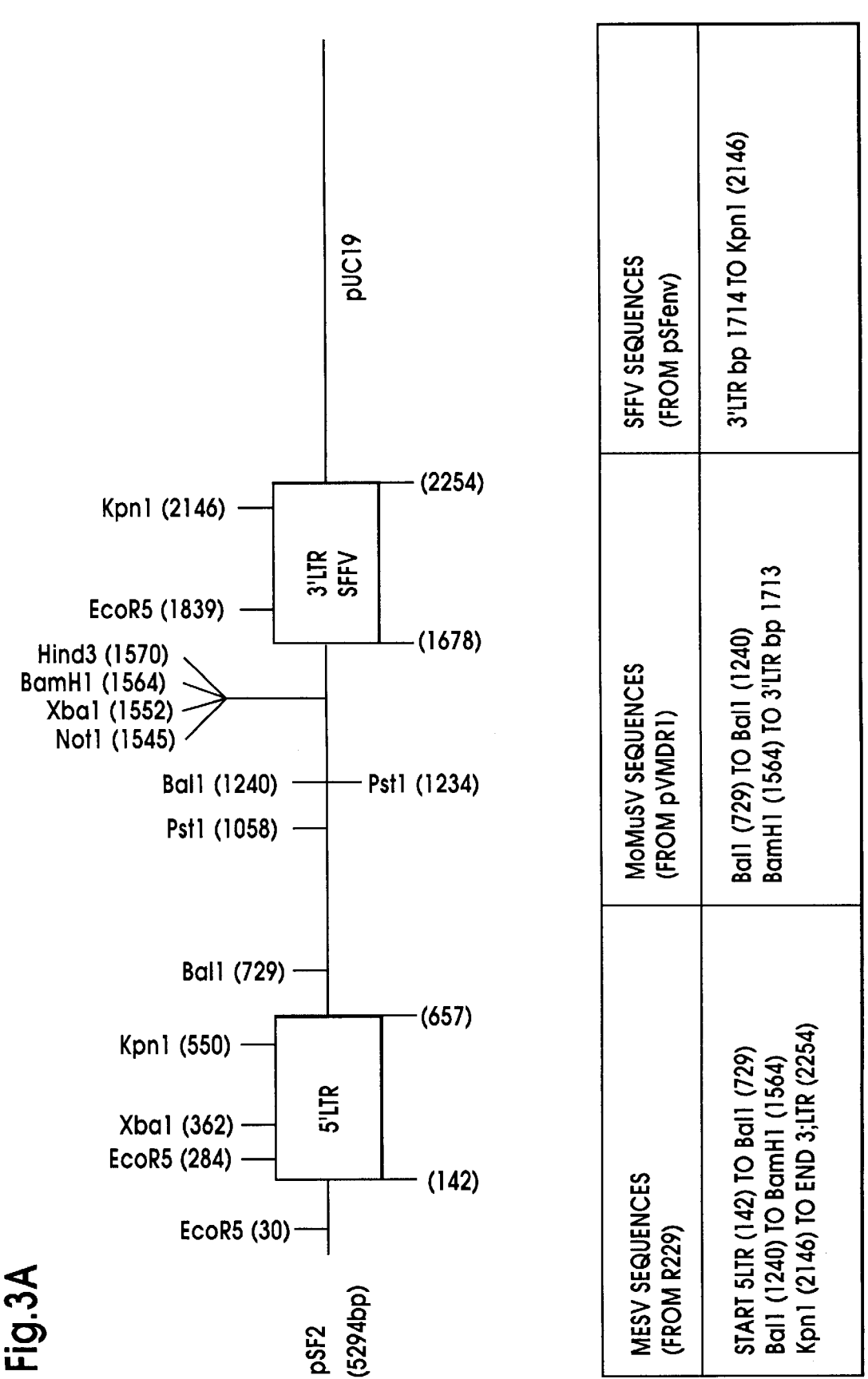
FIG. 3A shows the restriction map of pSF2
Figure 3B:
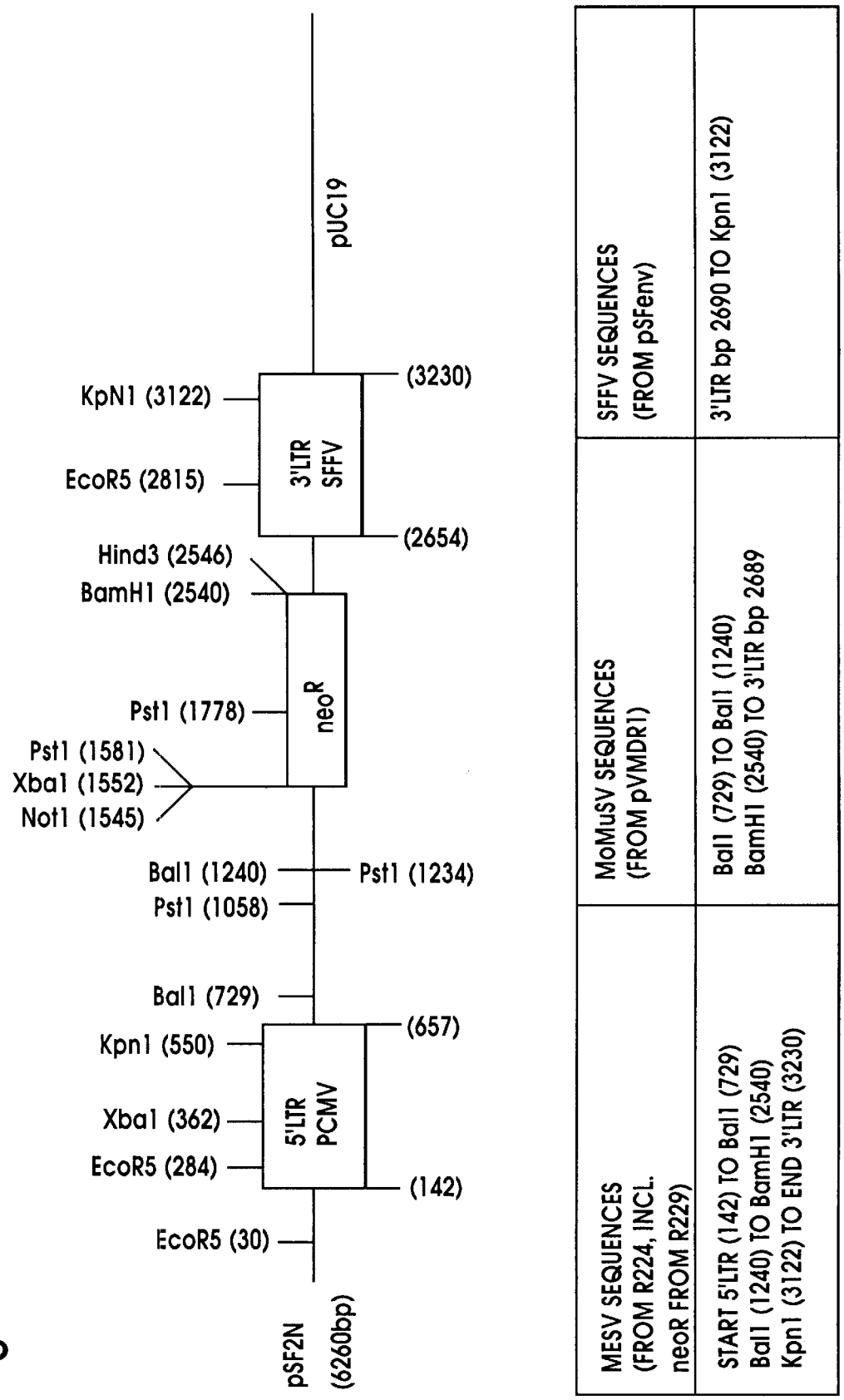
FIG. 3B shows the restriction map of pSF2N which corresponds to pSF2 after integration of the neo$^R$ gene
Figure 4A:
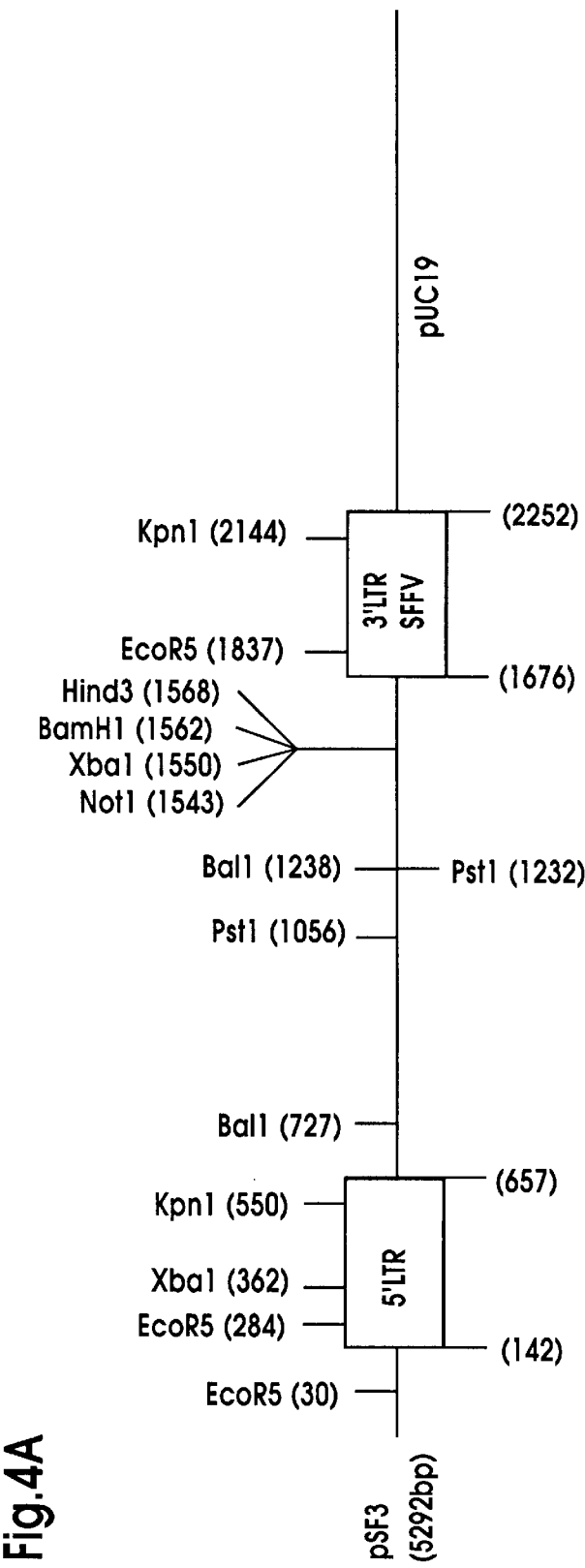
FIG. 4A shows the restriction map of pSF3
Figure 4B:
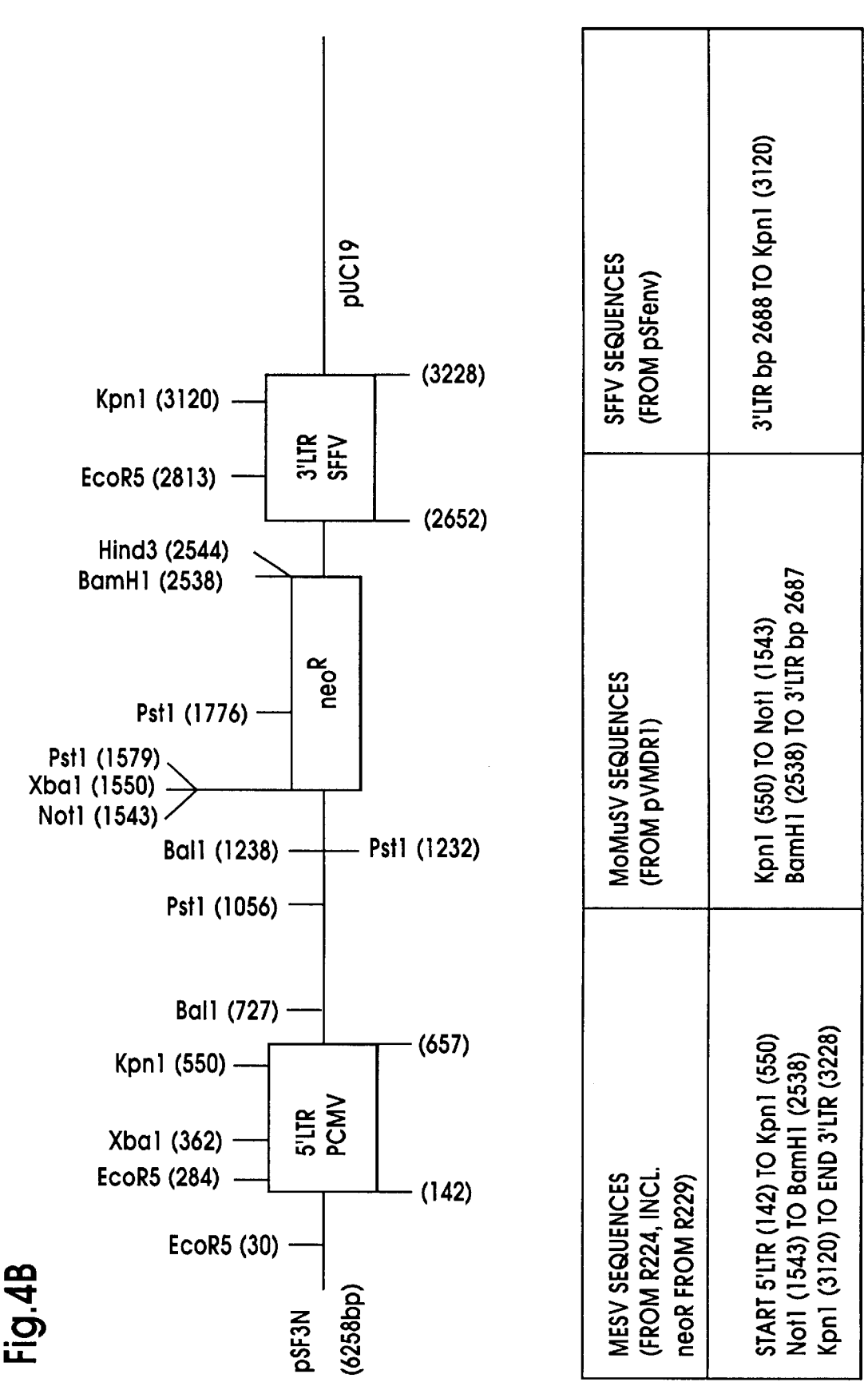
FIG. 4B shows the restriction map of pSF3N which corresponds to pSF3 after integration of the neo$^R$ gene
Figure 5A:
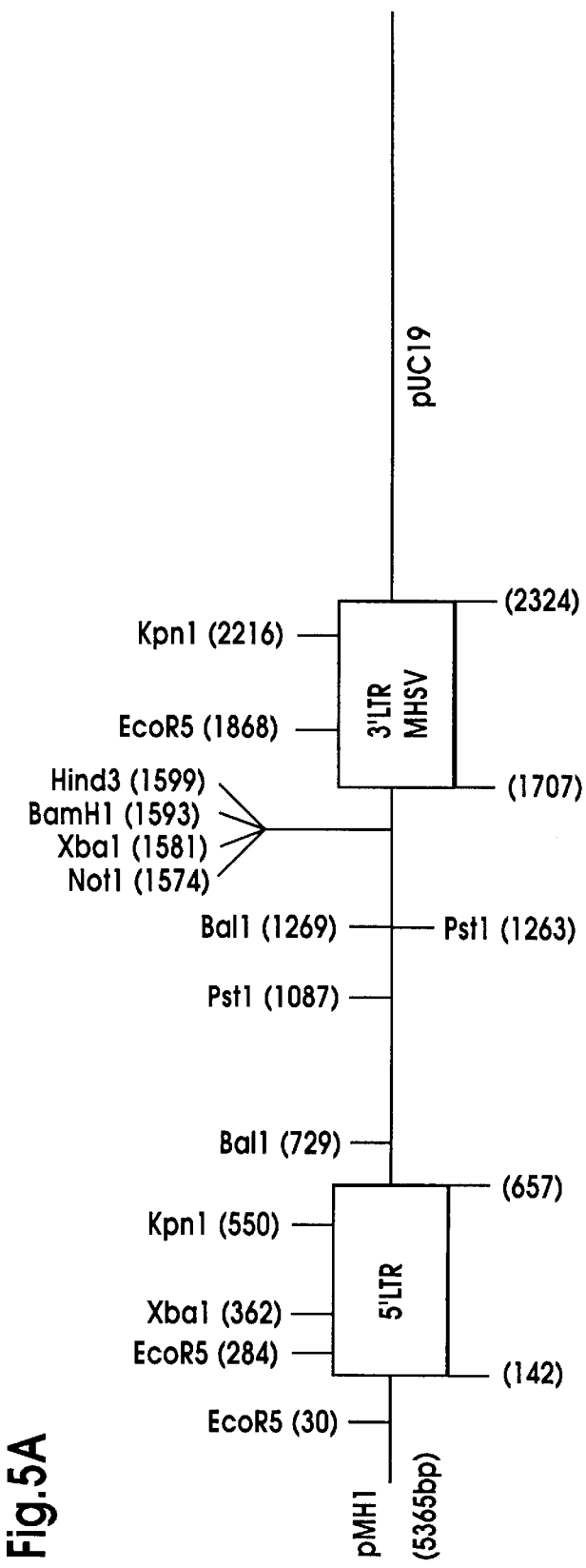
FIG. 5A shows the restriction map of pMH1
Figure 5B:
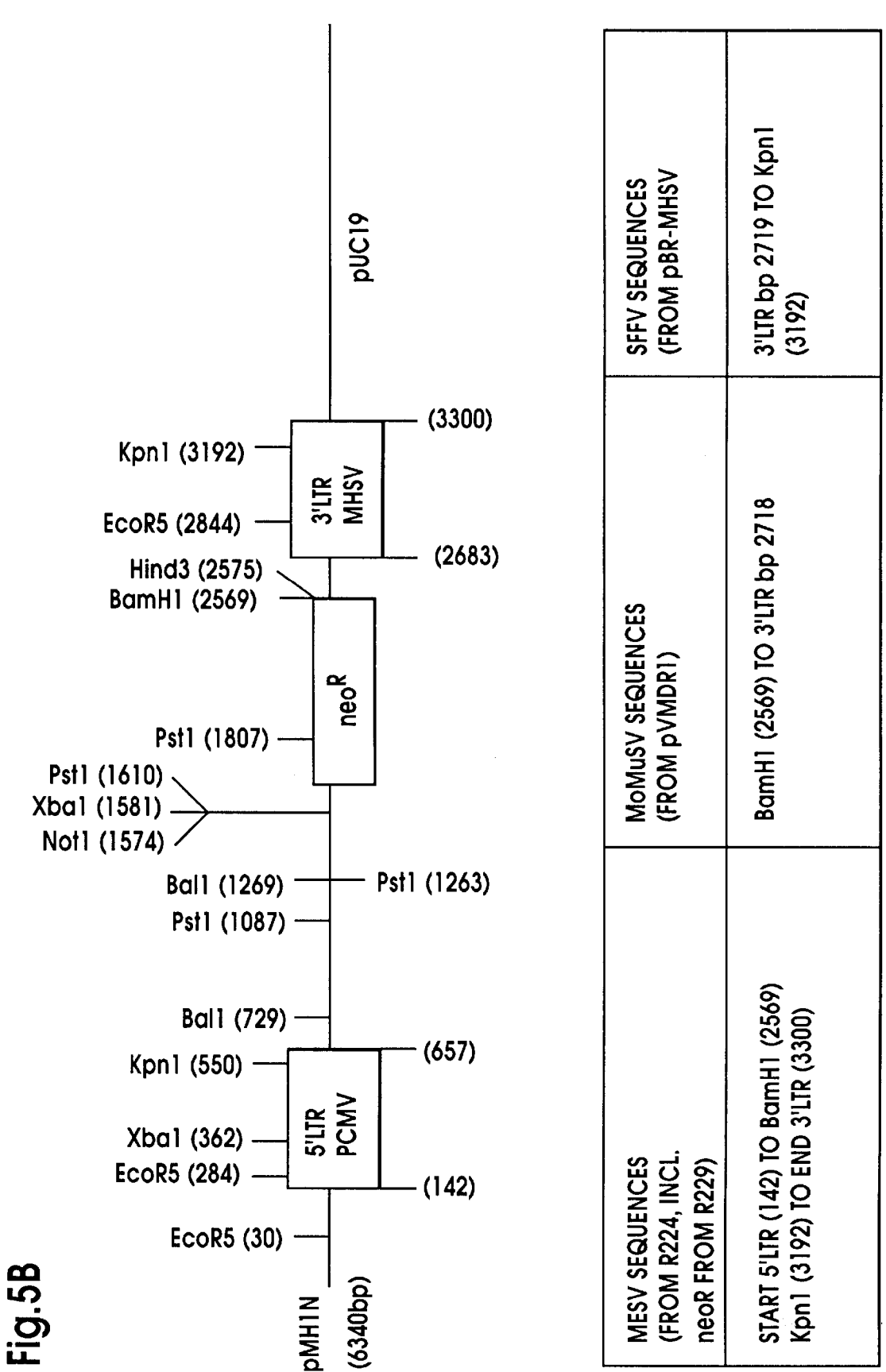
FIG. 5B shows the restriction map of pMH1N which corresponds to pMh1 after integration of the neo$^R$ gene.

Construction of insertion mutagenesis vectors capable of replication based on the Friend/MESV vector constructs according to the invention The construct example of an amphotropic Friend/MESV vector capable of replication was produced for insertion mutagenesis by cloning the gag-pol-env genes necessary for the retroviral replication into the Friend-/MESV vector pSF1 and pSF3 (see FIGS. 2A and 4A).

For this the entire 7.2 kb gag-pol-env gene cassette from pAM (Miller et al. (1985) (35)) was amplified with the help of the "expand long template PCR system" (Boehringer Mannheim, see also: W. M. Barns (1994) (36)) and incorporated into pSF1 and pSF3.

pAM represents a fusion construct from the ecotropic MoMuLV vector pMLV-K (gag-pol to the SalI cleavage site) and from the amphotropic virus 4070A vector p4070A (pol from the SalI cleavage site and env$^{amphotropic}$). The upper PCR primer was placed 60 bp upstream of the gag start codon (directly adjoining the PstI cleavage site), the lower PCR primer was directly placed at the end of the envamphotropic gene. The 7.2 kb gag-pol-env$^{amphotropic}$ PCR amplificate was incorporated uncleaved i.e. with blunt ends, into the vectors pSF1 and pSF3 that had been cleaved with PstI and HindIII and treated with Klenow enzyme in order to remove overhangs (Sambrook et al. (1989) (37)). The resulting vectors were named pSF1-AM, pSF3-AM and are in principle constructed as follows: 5 1'-LTR$^{MESV}$-PBS(-)$^{MESV}$-gag-pol-env$^{amphotropic}$-3'-LTR$^{SFFV}$ (pSF1-AM) and 5'-LTR$^{MESV}$-PBS(-)$^{MUSV}$-gag-pol-env$^{amphotropic}$-3'-LTR-$^{SFFV}$ (pSF3-AM).

After transfection in human or murine cells they are able to form replication-competent retroviruses (RCR) which can be used for insertion mutagenesis in haematopoietic stem and progenitor cells.

EXAMPLE 4

Construction of insertion mutagenesis vectors capable of replication based on MPSV/MESV vector constructs according to the invention In the vector MoMuLV-TAT (Hilberg, F. et al. Prog. Natl. Acad. Sci. USA 84 (1987) 5232–5236 (38) the NheI-KpnI fragment was replaced by the corresponding LTR fragment of MPSV (−416−+31). The resulting vector was named MP-CAT. This plasmid can be used as a reporter gene plasmid by expressing the chloroamphenicol transferase (CAT) gene under the control of the retroviral LTR fragment.

Figure 9:
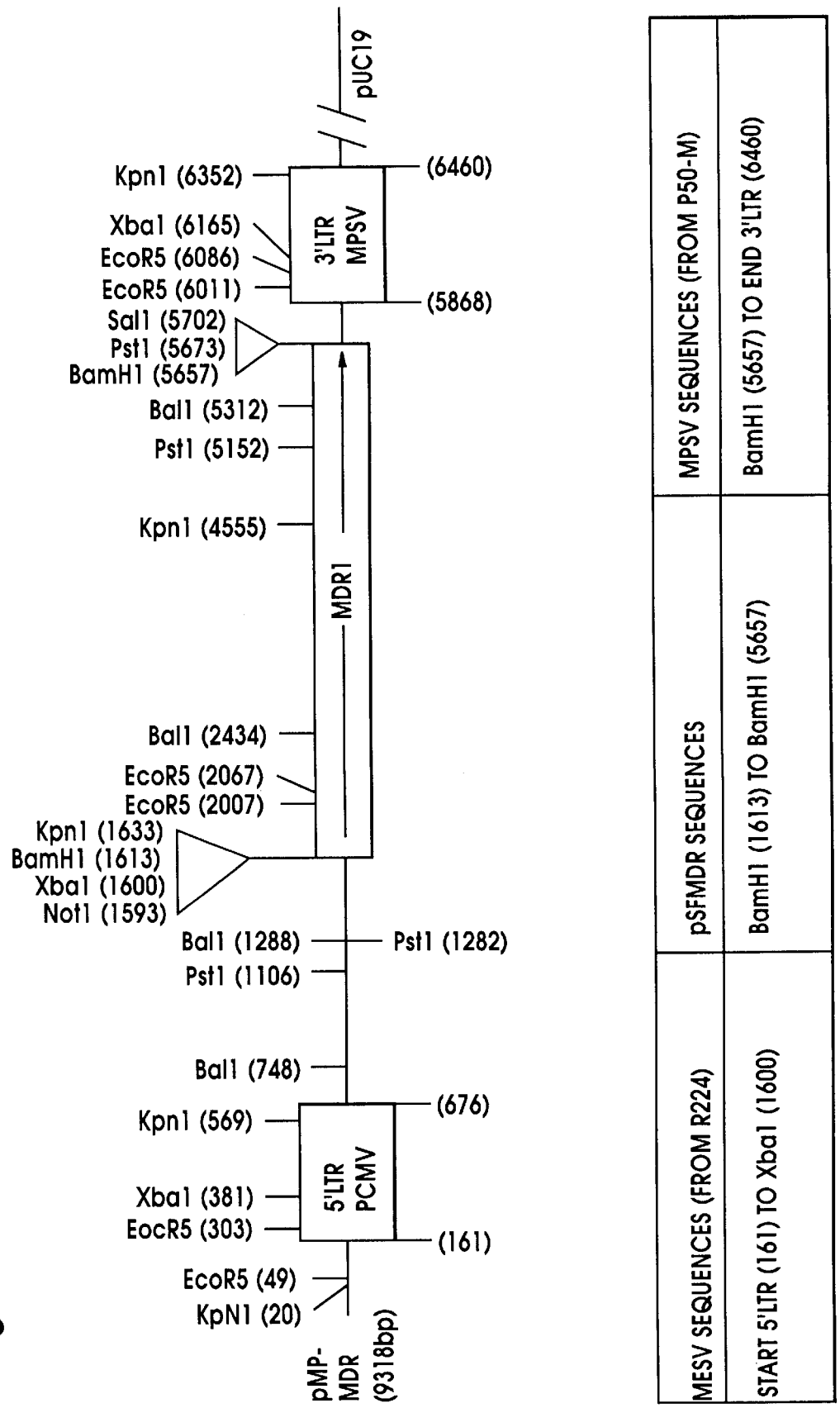
FIG. 9 shows the restriction map of pMP-MDR.

The vector P50-M is used as the MPSV/MESV base vector. This vector contains the MPSV-U3 in the 3'-LTR. It is a derivative of p5Gneo which contains a 537 bp long leader fragment of dl587rev (Grez M. et al., Proc. Natl. Acad. Sci. USA 87 (1990), 9202–9206 (39), Colicelli J. and Goff S. P., J. Virol. 57 (1987) 37–45 (40)). NeoR-env coding regions of p5Gneo were replaced by a polylinker from p Bluescript KS (Stratagene) and the AUG of gag was destroyed by point mutation. The mdr-1 cDNA was cut out from pMDR2000XS (base pair −138−+3878) as a SacI/SspI fragment (Chen C. et al., Cell 47 (1986) 381–389 (41)). After subcloning in p Bluescript II KS the cDNA was isolated as a BamHI fragment and p50-M was inserted. The vector produced in this way is named pMP-MDR. The sequence of p-MDR, pMP-MDR is shown in FIG. 9 and SEQ ID NO:6.

List of references (1) Miller A. D., Nature 357, 455–460 (1992)
(2) Mulligan R. C., Science 260, 926–932 (1993)
(3) Vile R. and Russell S. J., Gene Therapy 1, 88–98 (1994)
(4) Lu M. et al., Human Gene Therapy 5, 203–208 (1994)
(5) Palmer T. D. et al., Proc. Natl. Acad. Sci. U.S.A. 88, 1330–1334 (1991)
(6) Brenner M. K. et al., The Lancet 342, 1134–1137 (1993)
(7) Linemeyer D. L. et al., Proc. Natl. Acad. Sci. U.S.A. 78, 1401–1405 (1981)
(8) R. Petersen et al., Mol. Cell. Biol. 11, 1213–1221 (1991)
(9) Friel J. et al., J. Virol. 64, 369–378 (1990)
(10) Clark S. P. and Mak T. W., Nucl. Acid Res. 10, 3315–3330 (1982)
(11) Wolff L. et al., J. Virol. 53, 570–578 (1985)
(12) Bestwick R. K. et al., J. Virol. 51, 695–705 (1984)
(13) Koch W. et al., J. Virol. 49, 828–840 (1984)
(14) Adachi A. et al., J. Virol. 50, 813–821 (1984)
(15) Ostertag W. et al., Adv. Cancer Res. 48, 193–355 (1987)
(16) McKnight S. and Tijan R., Cell 46, 795–805 (1986)
(17) Ostertag W. et al., J. Virol. 33, 573–582 (1980)
(18) Stocking C. et al., Proc. Natl. Acad. Sci. U.S.A. 82, 5746–5750 (1985)
(19) Franz T. et al., Proc. Natl. Acad. Sci. U.S.A. 83, 3292–3296 (1986)
(20) Grez M. et al., J. Virol. 65, 4691–4698 (1991)
(21) Stocking C. et al., in Virus Strategies, ed. by W. Doerfler and P. Böhm, VCH Verlagsgesellschaft, Weinheim, Germany (1993)
(22) Grez M. et al., Proc. Natl. Acad. Sci. U.S.A. 87, 9202–9206 (1990)
(23) Colicelli J. and Goff S. P., J. Virol. 57, 37–45 (1987)
(24) Bilello J. A. et al., Virology 107, 331–344 (1980)
(25) Pastan I. et al., Proc. Nat. Acad. Sci. USA 85, 4486–4490 (1988)
(26) Ghattas I. R. et al., Mol. Cell. Biol. 11, 5848–5859 (1991)
(27) Miller A. D. and Rosman G. J., Biotechniques 7, 980–990 (1990)
(28) Anderson W. F., Human Gene Therapy 5, 1–2 (1994)
(29) Ohashi T. et al., Proc. Nat. Acad. Sci. USA 89, 11332–11336 (1992)
(30) T. Kitamura et al., J. Cell. Physiol. 140, 323–334 (1989)
(31) M. Kriegler, Gene Transfer and Expression, A Laboratory Manual, W. H. Freeman & Co., New York (1990), 47–55 and 161–164
(32) P. Artelt et al., Gene 99, 249–254 (1991)
(33) D. Johnson et al., Cell 47, 545–554 (1986)
(34) H. J. Kung et al., Current Topics in Microbiol. & Immunol. 171 (1991) 1–25
(35) A. D. Miller et al., Molecular and Cell Biology, Vol. 5, No. 3 (1985) 431–437
(36) W. M. Barns, Proc. Natl. Acad. Sci. USA 91 (1994) 2216–2220
(37) J. Sambrook et al., Molecular Cloning: A Laboratory Manual, second edition (1989), CSH Laboratory Press
(38) Hilberg, F. et al, Prog. Natl. Acad. Sci. USA 84 (1987) 5232 –5236

(39) Grez M. et al., Proc. Natl. Acad. Sci. USA 87 (1990), 9202–9206

(40) Colicelli J. und Goff S. P., J. Virol. 57 (1987) 37–45

(41) Chen C. et al., Cell 47 (1986) 381–389

We claim:

1. A retroviral vector hybrid comprising
   a) a 5'-LTR-comprising at least one U5 region or tRNA primer binding site wherein the region or site is selected from the group consisting of the U5 region of MESV, the tRNA primer binding site of MESV, the U5 region of MoMuSV, and the tRNA primer binding site of MoMuSV, and
   b) a 3'-LTR comprising the U3 and R regions from a Friend murine leukaemia virus (F-MuLV).

2. The vector hybrid of claim 1 further comprising the leader region of MESV.

3. The vector hybrid of claim 1, wherein the Friend murine leukaemia virus is selected from the group consisting of malignant histiosarcoma virus (MHSV), SFFVp Lilly-Steeves, SFFVa, Rauscher SSFV, F-muLVc157 and Friend-mink cell focus forming Virus.

4. The vector hybrid of claim 1, wherein the U3 and R regions in the 5'-LTR comprise the U3 and R regions from MPSV, MESV or PCMV.

5. The vector hybrid of claim 1, wherein the 5'-LTR comprises bp 142–657 from SEQ ID NO:1.

6. The vector hybrid of claim 1, wherein the 3'-LTR comprises bp 1707–2283 from SEQ ID NO:1.

7. The vector hybrid of claim 1 further comprising at least one gene that is heterologous to the retroviral vector and can be expressed in eukaryotic cells.

8. The vector hybrid of claim 1 which is replication-defective.

9. The vector hybrid of claim 1 which is replication-competent.

10. The vector hybrid of claim 7 wherein the heterologous gene is selected from the group consisting of a multiple drug resistance gene (MDR gene), an antibiotic resistance gene, a LNGFR gene, a cerebrosidase gene and the herpes simplex TK gene.

11. The vector of claim 10 wherein the heterologous gene is the neo$^R$ gene.

12. A vector hybrid selected from the group consisting of pSF1, pSF2, pSF3, and pHM1.

13. A process for the production of a retrovirally transduced eukaryotic cell which expresses an exogenous gene, said process comprising transducing a eukaryotic cell with a retroviral vector virus, which virus comprises a) at least one U5 region or tRNA primer binding site wherein the region or site is selected from the group consisting of the U5 region of MESV, the tRNA primer binding site of MESV, the U5 region of MoMuSV, and the tRNA primer binding site of MoMuSV, and b) a 3'-LTR comprising the U3 and R regions from a Friend murine leukaemia virus (F-MuLV).

14. The process as claimed in claim 13 wherein the retroviral vector virus is replication defective.

15. The process as claimed in claim 13 wherein the eukaryotic cells is a haematopoietic stem cells.

16. An eukaryotic cell obtained by the process of transducing a eukaryotic cell with a retroviral vector virus comprising a) at least one U5 region or tRNA primer binding site wherein the region or site is selected from the group consisting of the U5 region of MESV, the tRNA primer binding site of MESV, the U5 region of MoMuSV, and the tRNA primer binding site of MoMuSV, and b) a 3'-LTR comprising the U3 and R regions from a Friend murine leukaemia virus (F-MuLV).

17. The cell of claim 16 wherein the F-MuLV is selected from the group consisting of malignant histiosarcoma virus (MHSV), SFFVp Lilly-Steeves, SFFVa, Rauscher SSFV, F-muLVc157 and Friend-mink cell focus forming virus.

18. The cell of claim 16 wherein the vector further comprises the leader region of MESV.

19. The cell of claim 16 wherein the retroviral vector virus is replication defective.

20. A replication defective infectious virus particle comprising a retroviral RNA genome, wherein the genome comprises a) at least one U5 region or tRNA primer binding site selected from the group consisting of the U5 region of MESV, the tRNA primer binding site of MESV, the U5 region of MoMuSV, and the tRNA primer binding site of MoMuSV, and b) further comprises a packaging function, a gene which is heterologous to the virus and can be expressed in the eukaryotic cell, and U3 and R from a Friend murine leukaemia virus (F-MuLV), but c) does not comprise active gag, env and pol sequences at the 3' end.

21. A process for the production of a replication defective infectious virus particle comprising a) transfecting a eukaryotic helper cell which has the helper functions gag, env and pol with a vector hybrid comprising i) at least one U5 region or tRNA primer binding site wherein the region or site is selected from the group consisting of the U5 region of MESV, the tRNA primer binding site of MESV, the U5 region of MoMuSV, and the tRNA primer binding site of MoMuSV, and ii) a 3'-LTR comprising the U3 and R regions from a Friend murine leukaemia virus (F-MuLV), b) producing the RNA corresponding to the DNA of the vector hybrid as the virus genome in the cell, c) packaging the virus genome into the replication deficient empty virus envelopes formed in the cell, and d) isolating the infectious virus particles which contain said virus genome.

22. The process of claim 21 wherein the F-MuLV is selected from the group consisting of malignant histiosarcoma virus (MHSV), SFFVp Lilly-Steeves, SFFVa, Rauscher SFFV, F-muLVc 157 and Friend-mink cell focus forming virus.

23. The process of claim 21 wherein the vector hybrid further comprises the leader region of MESV.

24. A retroviral vector hybrid comprising a) the U5 region and tRNA primer binding site of MESV as the U5 region and the tRNA primer binding site in the leader region, and b) the U3 and R regions from myeloproliferative sarcoma virus (MPSV) as the U3 and R regions in the 3'-LTR.

25. A process for the production of a retrovirally transduced eukaryotic cell comprising an exogenous gene, wherein the eukaryotic cell is transduced with the retroviral vector virus comprising:

a) the U5 region and/or tRNA primer binding site of MESV as the U5 region and/or tRNA primer binding site in the leader region, b) the U3 and R regions from myeloproliferative sarcoma virus (MPSV) as the U3 and R regions in the 3'-LTR and c) the said exogenous gene.

26. A replication defective infectious virus particle comprising retroviral RNA as the genome, wherein the genome comprises the U5 regions and/or tRNA primer binding site of MESV as the U5 region and/or tRNA primer binding site, a packaging function and a gene which is heterologous for the virus and can be expressed in the eukaryotic cell, and U3 and R from the myeloproliferative sarcoma virus (MPSV) but no active gag, env and pol sequences at the 3' end.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 5323 base pairs
( B ) TYPE: nucleic acid
( C ) STRANDEDNESS: double
( D ) TOPOLOGY: circular ( i i ) MOLECULE TYPE: DNA ( x i ) SEQUENCE DESCRIPTION: SEQ ID NO: 1:

```
CGATTAGTCC   AATTTGTTAA   AGACAGGATA   TCAGGTGGTC   CAGGCTCTAG   TTTTGACTCA     60
ACAATATCAC   CAGCTGAAGC   CTATAGAGTA   CGAGCCATAG   ATAGAATAAA   AGATTTTATT    120
TAGTCTCCAG   AAAAAGGGGG   GAATGAAAGA   CCCCACCTGT   AGGTTTGGCA   AGCTAGCTTA    180
AGTAACGCCA   TTTTGCAAGG   CATGGAAAAT   ACATAACTGA   GAATAGAGAA   GTTCAGATCA    240
AGGTTAGGAA   CAGAGAGACA   GCAGAATATG   GGCCAAACAG   GATATCTGTG   GTAAGCAGTT    300
CCTGCCCCGC   TCAGGGCCAA   GAACAGATGG   TCCCCAGATG   CGGTCCCGCC   CTCAGCAGTT    360
TCTAGAGAAC   CATCAGATGT   TTCCAGGGTG   CCCCAAGGAC   CTGAAAATGA   CCCTGTGCCT    420
TATTTGAACT   AACCAATCAG   TTCGCTTCTC   GCTTCTGTTC   GCGCGCTTCT   GCTCCCGAG     480
CTCAATAAAA   GAGCCCACAA   CCCCTCACTC   GGCGCGCCAG   TCCTCCGATT   GACTGCGTCG    540
CCCGGGTACC   CGTATTCCCA   ATAAAGCCTC   TTGCTGTTTG   CATCCGAATC   GTGGACTCGC    600
TGATCCTTGG   GAGGGTCTCC   TCAGATTGAT   TGACTGCCCA   CCTCGGGGGT   CTTTCATTTG    660
GAGGTTCCAC   CGAGATTTGG   AGACCCCAGC   CCAGGGACCA   CCGACCCCC    CGCCGGGAGG    720
TAAGCTGGCC   AGCGGTCGTT   TCGTGTCTGT   CTCTGTCTTT   GTGCGTGTTT   GTGCCGGCAT    780
CTAATGTTTG   CGCCTGCGTC   TGTACTAGTT   GGCTAACTAG   ATCTGTATCT   GGCGGTCCCG    840
CGGAAGAACT   GACGAGTTCG   TATTCCCGGC   CGCAGCCCCT   AGGAGACGTC   CCAGCGGCCT    900
CGGGGGCCCG   TTTTGTGGCC   CGTTCTGTGT   CGTTAACCAC   CGAGTCGGA    CTTTTTGGAG    960
CTCCGCCACT   GTCCGAGGGG   TACGTGGCTT   TGTTGGGGGA   CGAGAGACAG   AGACACTTCC   1020
CGCCCCCGTC   TGAATTTTTG   CTTTCGGTTT   TACGCCGAAA   CCGCGCCGCG   CGTCTTGTCT   1080
GCTGCAGCAT   CGTTCTGTGT   TGTCTCTGTC   TGACTGTGTT   TCTGTATTTG   TCTGAAAATT   1140
AGGGCCAGAC   TGTTACCACT   CCCTTAAGTT   TGACCTTAGA   TCACTGGAAA   GATGTCGAGC   1200
GGATCGCTCA   CAACCAGTCG   GTAGATGTCA   AGAAGAGACG   ATGGGTTACC   TTCTGCTCTG   1260
CAGAATGGCC   AACCTTTAAC   GTCGGATGGC   CGCGAGACGG   CACCTTTAAC   CGAGACCTCA   1320
TCACCCAGGT   TAAGATCAAG   GTCTTTTCAC   CTGGCCCGCA   TGGACACCCA   GACCAGGTCC   1380
CCTACATCGT   GACCTGGGAA   GCCTTGGCTT   TTGACCCCCC   TCCCTGGGTC   AAGCCCTTTG   1440
TACACCCTAA   GCCTCCGCCT   CCTCTTCCTC   CATCCGCCCC   GTCTCTCCCC   CTTGAACCTC   1500
CTCTTTCGAC   CCCGCCTCGA   TCCTCCCTTT   ATCCAGCCCT   CACTCCTTCT   CTAGGCGGCT   1560
CCACCGCGGT   GGCGGCCGCT   CTAGAACTAG   TGGATCCAAG   CTTATCGATA   GGCCTAGGCC   1620
TATCGATAGG   CCTAGGCCTA   TCGATAGGCC   TAACACGAGC   CATAGATAGA   ATAAAGATT    1680
TTATTTAGTC   TCCAGAAAAA   GGGGGGAATG   AAAGACCCCA   CCTGTAGGTT   TGGCAAGCTA   1740
```

```
GAGTCGCTTA  GCCTGATAGC  CGCAGTAACG  CCATTTTGCA  AGGCATGGAA  AAATACCAAA    1800

CCAAGAATAG  GGAAGTTCAG  ATCAAGGGCG  GGTACATGAA  AATAGCTAAC  GTTGGGCCAA    1860

ACAGGATATC  TGCGGTGAGC  AGTTTCGGCC  CCGGCCCGGG  GCAAGAACAG  ATGGTCACCG    1920

CAGTTTCGGC  CCCGGCCCGA  GGCCAAGAAC  AGATGGTCCC  CAGATATGGC  CCAACCCTCA    1980

GCAGTTTCTT  AAGACCCATC  AGATGTTTCC  AGGCTCCCCC  AAGGACCTGA  AATGACCCTG    2040

CGCCTTATTT  GAATTAACCA  ATCAGCCTGC  TTCTCGCTTC  TGTTCGCGCG  CTTCTGCTTC    2100

CCGAGCTCTA  TAAAGAGCT   CACAACCCCT  CACTCGGCGC  GCCAGTCCTC  CGATTGACTG    2160

AGTCGCCCGG  GTACCCGTGT  TCTCAATAAA  CCCTCTTGCA  GTTGCATCCG  ACTCGTGGTC    2220

TCGCTGTTCC  TTGGGAGGGT  CTCCTCTGAG  TGATTGACTA  CCCGTCAGCG  GGGGTCTTTC    2280

AGTTTCTCCC  ACCTACACAG  GTCTCACTAA  CATTCCTGAT  GTGCCGCAGG  GACTCCGTCA    2340

GCCCGGTTTG  TGTTTATAAT  AAAATGCAAG  AACAGTGTTC  CCTTCAAGCC  AGACTACATC    2400

CTGACTCTCG  GCTTTATAAA  AGAATGTTGA  AGGGCTCTGT  GGACTATCTG  CCACACGACT    2460

TTTAAGATTT  TTATGCCTCC  TGGATGAGGG  ATTTAGTCAA  TCTATCCTCG  TCTATTTTGC    2520

TGGCTTCTCC  GTATTTTAAA  TTTCTAGTTT  GCACTCCCTT  CCTGAGAGCA  CGGCGATTGC    2580

AGAGTAGTTA  ATACTCTGAG  GGCAGGCTTC  TGTGAAAAGG  TTGCCTGGGC  TCAGTGTGAG    2640

ATTTTGCCAT  AAAAAGGGGT  CCTGCCCCTG  TGTACAGACA  GATCGGAATC  TAGAGTGCAT    2700

ACTCAGAGTC  CCCGCGGTTC  CGGGGCTCTG  ATCTCAGGGC  ATCTTTGCCT  AGAGATCCTC    2760

TACGCCGGAC  GCATCGTGGC  CGGCATCACC  GGCGCCACAG  GTGCGGTTGC  TGGCGCCTAT    2820

ATCGCCGACA  TCACCGATGG  GGAAGATCGG  GCTCGCCACT  TCGGGCTCAT  GAGCGCTTGT    2880

TTCGGCGTGG  GTATGGTGGC  AGGCCCCGTG  GCCGGGGAC   TGTTGGGCGC  CATCTCCTTG    2940

CATGCACCAT  TCCTTGCGGC  GGCGGTGCTC  AACGGCCTCA  ACCTACTACT  GGGCTGCTTC    3000

CTAATGCAGG  AGTCGCATAA  GGGAGAGCGT  CCTGCATTAA  TGAATCGGCC  AACGCGCGGG    3060

GAGAGGCGGT  TTGCGTATTG  GGCGCTCTTC  CGCTTCCTCG  CTCACTGACT  CGCTGCGCTC    3120

GGTCGTTCGG  CTGCGGCGAG  CGGTATCAGC  TCACTCAAAG  GCGGTAATAC  GGTTATCCAC    3180

AGAATCAGGG  GATAACGCAG  GAAAGAACAT  GTGAGCAAAA  GGCCAGCAAA  AGGCCAGGAA    3240

CCGTAAAAAG  GCCGCGTTGC  TGGCGTTTTT  CCATAGGCTC  CGCCCCCCTG  ACGAGCATCA    3300

CAAAAATCGA  CGCTCAAGTC  AGAGGTGGCG  AAACCCGACA  GGACTATAAA  GATACCAGGC    3360

GTTTCCCCCT  GGAAGCTCCC  TCGTGCGCTC  TCCTGTTCCG  ACCCTGCCGC  TTACCGGATA    3420

CCTGTCCGCC  TTTCTCCCTT  CGGGAAGCGT  GGCGCTTTCT  CAATGCTCAC  GCTGTAGGTA    3480

TCTCAGTTCG  GTGTAGGTCG  TTCGCTCCAA  GCTGGGCTGT  GTGCACGAAC  CCCCCGTTCA    3540

GCCCGACCGC  TGCGCCTTAT  CCGGTAACTA  TCGTCTTGAG  TCCAACCCGG  TAAGACACGA    3600

CTTATCGCCA  CTGGCAGCAG  CCACTGGTAA  CAGGATTAGC  AGAGCGAGGT  ATGTAGGCGG    3660

TGCTACAGAG  TTCTTGAAGT  GGTGGCCTAA  CTACGGCTAC  ACTAGAAGGA  CAGTATTTGG    3720

TATCTGCGCT  CTGCTGAAGC  CAGTTACCTT  CGGAAAAAGA  GTTGGTAGCT  CTTGATCCGG    3780

CAAACAAACC  ACCGCTGGTA  GCGGTGGTTT  TTTTGTTTGC  AAGCAGCAGA  TTACGCGCAG    3840

AAAAAAGGA   TCTCAAGAAG  ATCCTTTGAT  CTTTTCTACG  GGGTCTGACG  CTCAGTGGAA    3900

CGAAAACTCA  CGTTAAGGGA  TTTTGGTCAT  GAGATTATCA  AAAAGGATCT  TCACCTAGAT    3960

CCTTTTAAAT  TAAAAATGAA  GTTTTAAATC  AATCTAAAGT  ATATATGAGT  AAACTTGGTC    4020

TGACAGTTAC  CAATGCTTAA  TCAGTGAGGC  ACCTATCTCA  GCGATCTGTC  TATTTCGTTC    4080

ATCCATAGTT  GCCTGACTCC  CCGTCGTGTA  GATAACTACG  ATACGGGAGG  GCTTACCATC    4140
```

```
TGGCCCCAGT  GCTGCAATGA  TACCGCGAGA  CCCACGCTCA  CCGGCTCCAG  ATTTATCAGC    4200

AATAAACCAG  CCAGCCGGAA  GGGCCGAGCG  CAGAAGTGGT  CCTGCAACTT  TATCCGCCTC    4260

CATCCAGTCT  ATTAATTGTT  GCCGGGAAGC  TAGAGTAAGT  AGTTCGCCAG  TTAATAGTTT    4320

GCGCAACGTT  GTTGCCATTG  CTACAGGCAT  CGTGGTGTCA  CGCTCGTCGT  TTGGTATGGC    4380

TTCATTCAGC  TCCGGTTCCC  AACGATCAAG  GCGAGTTACA  TGATCCCCCA  TGTTGTGCAA    4440

AAAAGCGGTT  AGCTCCTTCG  GTCCTCCGAT  CGTTGTCAGA  AGTAAGTTGG  CCGCAGTGTT    4500

ATCACTCATG  GTTATGGCAG  CACTGCATAA  TTCTCTTACT  GTCATGCCAT  CCGTAAGATG    4560

CTTTTCTGTG  ACTGGTGAGT  ACTCAACCAA  GTCATTCTGA  GAATAGTGTA  TGCGGCGACC    4620

GAGTTGCTCT  TGCCCGGCGT  CAATACGGGA  TAATACCGCG  CCACATAGCA  GAACTTTAAA    4680

AGTGCTCATC  ATTGGAAAAC  GTTCTTCGGG  GCGAAAACTC  TCAAGGATCT  TACCGCTGTT    4740

GAGATCCAGT  TCGATGTAAC  CCACTCGTGC  ACCCAACTGA  TCTTCAGCAT  CTTTTACTTT    4800

CACCAGCGTT  TCTGGGTGAG  CAAAAACAGG  AAGGCAAAAT  GCCGCAAAAA  AGGGAATAAG    4860

GGCGACACGG  AAATGTTGAA  TACTCATACT  CTTCCTTTTT  CAATATTATT  GAAGCATTTA    4920

TCAGGGTTAT  TGTCTCATGA  GCGGATACAT  ATTTGAATGT  ATTTAGAAAA  ATAAACAAAT    4980

AGGGGTTCCG  CGCACATTTC  CCCGAAAAGT  GCCACCTGAC  GTCTAAGAAA  CCATTATTAT    5040

CATGACATTA  ACCTATAAAA  ATAGGCGTAT  CACGAGGCCC  TTTCGTCTCG  CGCGTTTCGG    5100

TGATGACGGT  GAAAACCTCT  GACACATGCA  GCTCCCGGAG  ACGGTCACAG  CTTGTCTGTA    5160

AGCGGATGCC  GGGAGCAGAC  AAGCCCGTCA  GGGCGCGTCA  GCGGGTGTTG  GCGGGTGTCG    5220

GGGCTGGCTT  AACTATGCGG  CATCAGAGCA  GATTGTACTG  AGAGTGCACC  ATATGCGGTG    5280

TGAAATACCG  CACAGATGCG  TAAGGAGAAA  ATACCGCATC  AGG                       5323
```

(2) INFORMATION FOR SEQ ID NO: 2:

(i) SEQUENCE CHARACTERISTICS:
        (A) LENGTH: 5294 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO: 2:

```
CGATTAGTCC  AATTTGTTAA  AGACAGGATA  TCAGGTGGTC  CAGGCTCTAG  TTTTGACTCA      60

ACAATATCAC  CAGCTGAAGC  CTATAGAGTA  CGAGCCATAG  ATAGAATAAA  AGATTTTATT     120

TAGTCTCCAG  AAAAAGGGGG  GAATGAAAGA  CCCCACCTGT  AGGTTTGGCA  AGCTAGCTTA     180

AGTAACGCCA  TTTTGCAAGG  CATGGAAAAT  ACATAACTGA  GAATAGAGAA  GTTCAGATCA     240

AGGTTAGGAA  CAGAGAGACA  GCAGAATATG  GGCCAAACAG  GATATCTGTG  GTAAGCAGTT     300

CCTGCCCCGC  TCAGGGCCAA  GAACAGATGG  TCCCCAGATG  CGGTCCCGCC  CTCAGCAGTT     360

TCTAGAGAAC  CATCAGATGT  TTCCAGGGTG  CCCCAAGGAC  CTGAAAATGA  CCCTGTGCCT     420

TATTTGAACT  AACCAATCAG  TTCGCTTCTC  GCTTCTGTTC  GCGCGCTTCT  GCTCCCCGAG     480

CTCAATAAAA  GAGCCCACAA  CCCCTCACTC  GGCGCGCCAG  TCCTCCGATT  GACTGCGTCG     540

CCCGGGTACC  CGTATTCCCA  ATAAAGCCTC  TTGCTGTTTG  CATCCGAATC  GTGGACTCGC     600

TGATCCTTGG  GAGGGTCTCC  TCAGATTGAT  TGACTGCCCA  CCTCGGGGGT  CTTTCATTTG     660

GAGGTTCCAC  CGAGATTTGG  AGACCCCAGC  CCAGGGACCA  CCGACCCCCC  CGCCGGGAGG     720

TAAGCTGGCC  AGCAACTTAT  CTGTGTCTGT  CCGATTGTCT  AGTGTCTATG  TTTGATGTTA     780
```

```
TGCGCCTGCG  TCTGTACTAG  TTAGCTAACT  AGCTCTGTAT  CTGGCGGACC  CGTGGTGGAA   840
CTGACGAGTT  CTGAACACCC  GGCCGCAACC  CTGGGAGACG  TCCCAGGGAC  TTTGGGGGCC   900
GTTTTTGTGG  CCCGACCTGA  GGAAGGGAGT  CGATGTGGAA  TCCGACCCCG  TCAGGATATG   960
TGGTTCTGGT  AGGAGACGAG  AACCTAAAAC  AGTTCCCGCC  TCCGTCTGAA  TTTTTGCTTT  1020
CGGTTTGGAA  CCGAAGCCGC  GCGTCTTGTC  TGCTGCAGCA  TCGTTCTGTG  TTGTCTCTGT  1080
CTGACTGTGT  TTCTGTATTT  GTCTGAAAAT  TAGGGCCAGA  CTGTTACCAC  TCCCTTAAGT  1140
TTGACCTTAG  ATCACTGGAA  AGATGTCGAG  CGGATCGCTC  ACAACCAGTC  GGTAGATGTC  1200
AAGAAGAGAC  GATGGGTTAC  CTTCTGCTCT  GCAGAATGGC  CAACCTTTAA  CGTCGGATGG  1260
CCGCGAGACG  GCACCTTTAA  CCGAGACCTC  ATCACCCAGG  TTAAGATCAA  GGTCTTTTCA  1320
CCTGGCCCGC  ATGGACACCC  AGACCAGGTC  CCCTACATCG  TGACCTGGGA  AGCCTTGGCT  1380
TTTGACCCCC  CTCCCTGGGT  CAAGCCCTTT  GTACACCCTA  AGCCTCCGCC  TCCTCTTCCT  1440
CCATCCGCCC  CGTCTCTCCC  CCTTGAACCT  CCTCTTTCGA  CCCCGCCTCG  ATCCTCCCTT  1500
TATCCAGCCC  TCACTCCTTC  TCTAGGCGGC  TCCACCGCGG  TGGCGGCCGC  TCTAGAACTA  1560
GTGGATCCAA  GCTTATCGAT  AGGCCTAGGC  CTATCGATAG  GCCTAGGCCT  ATCGATAGGC  1620
CTAACACGAG  CCATAGATAG  AATAAAAGAT  TTTATTTAGT  CTCCAGAAAA  AGGGGGGAAT  1680
GAAAGACCCC  ACCTGTAGGT  TTGGCAAGCT  AGAGTCGCTT  AGCCTGATAG  CCGCAGTAAC  1740
GCCATTTTGC  AAGGCATGGA  AAAATACCAA  ACCAAGAATA  GGGAAGTTCA  GATCAAGGGC  1800
GGGTACATGA  AAATAGCTAA  CGTTGGGCCA  AACAGGATAT  CTGCGGTGAG  CAGTTTCGGC  1860
CCCGGCCCGG  GGCAAGAACA  GATGGTCACC  GCAGTTTCGG  CCCCGGCCCG  AGGCCAAGAA  1920
CAGATGGTCC  CCAGATATGG  CCCAACCCTC  AGCAGTTTCT  TAAGACCCAT  CAGATGTTTC  1980
CAGGCTCCCC  CAAGGACCTG  AAATGACCCT  GCGCCTTATT  TGAATTAACC  AATCAGCCTG  2040
CTTCTCGCTT  CTGTTCGCGC  GCTTCTGCTT  CCCGAGCTCT  ATAAAAGAGC  TCACAACCCC  2100
TCACTCGGCG  CGCCAGTCCT  CCGATTGACT  GAGTCGCCCG  GGTACCCGTG  TTCTCAATAA  2160
ACCCTCTTGC  AGTTGCATCC  GACTCGTGGT  CTCGCTGTTC  CTTGGGAGGG  TCTCCTCTGA  2220
GTGATTGACT  ACCCGTCAGC  GGGGGTCTTT  CAGTTTCTCC  CACCTACACA  GGTCTCACTA  2280
ACATTCCTGA  TGTGCCGCAG  GGACTCCGTC  AGCCCGGTTT  GTGTTTATAA  TAAAATGCAA  2340
GAACAGTGTT  CCCTTCAAGC  CAGACTACAT  CCTGACTCTC  GGCTTTATAA  AAGAATGTTG  2400
AAGGGCTCTG  TGGACTATCT  GCCACACGAC  TTTTAAGATT  TTTATGCCTC  CTGGATGAGG  2460
GATTTAGTCA  ATCTATCCTC  GTCTATTTTG  CTGGCTTCTC  CGTATTTTAA  ATTTCTAGTT  2520
TGCACTCCCT  TCCTGAGAGC  ACGGCGATTG  CAGAGTAGTT  AATACTCTGA  GGGCAGGCTT  2580
CTGTGAAAAG  GTTGCCTGGG  CTCAGTGTGA  GATTTTGCCA  TAAAAGGGG  TCCTGCCCCT  2640
GTGTACAGAC  AGATCGGAAT  CTAGAGTGCA  TACTCAGAGT  CCCCGCGGTT  CCGGGGCTCT  2700
GATCTCAGGG  CATCTTTGCC  TAGAGATCCT  CTACGCCGGA  CGCATCGTGG  CCGGCATCAC  2760
CGGCGCCACA  GGTGCGGTTG  CTGGCGCCTA  TATCGCCGAC  ATCACCGATG  GGAAGATCG   2820
GGCTCGCCAC  TTCGGGCTCA  TGAGCGCTTG  TTTCGGCGTG  GGTATGGTGG  CAGGCCCCGT  2880
GGCCGGGGGA  CTGTTGGGCG  CCATCTCCTT  GCATGCACCA  TTCCTTGCGG  CGGCGGTGCT  2940
CAACGGCCTC  AACCTACTAC  TGGGCTGCTT  CCTAATGCAG  GAGTCGCATA  AGGGAGAGCG  3000
TCCTGCATTA  ATGAATCGGC  CAACGCGCGG  GGAGAGGCGG  TTTGCGTATT  GGGCGCTCTT  3060
CCGCTTCCTC  GCTCACTGAC  TCGCTGCGCT  CGGTCGTTCG  GCTGCGGCGA  GCGGTATCAG  3120
CTCACTCAAA  GGCGGTAATA  CGGTTATCCA  CAGAATCAGG  GGATAACGCA  GGAAAGAACA  3180
```

-continued

| | | | | | | |
|---|---|---|---|---|---|---|
|TGTGAGCAAA|AGGCCAGCAA|AAGGCCAGGA|ACCGTAAAAA|GGCCGCGTTG|CTGGCGTTTT|3240|
|TCCATAGGCT|CCGCCCCCCT|GACGAGCATC|ACAAAAATCG|ACGCTCAAGT|CAGAGGTGGC|3300|
|GAAACCCGAC|AGGACTATAA|AGATACCAGG|CGTTTCCCCC|TGGAAGCTCC|CTCGTGCGCT|3360|
|CTCCTGTTCC|GACCCTGCCG|CTTACCGGAT|ACCTGTCCGC|CTTTCTCCCT|TCGGGAAGCG|3420|
|TGGCGCTTTC|TCAATGCTCA|CGCTGTAGGT|ATCTCAGTTC|GGTGTAGGTC|GTTCGCTCCA|3480|
|AGCTGGGCTG|TGTGCACGAA|CCCCCCGTTC|AGCCCGACCG|CTGCGCCTTA|TCCGGTAACT|3540|
|ATCGTCTTGA|GTCCAACCCG|GTAAGACACG|ACTTATCGCC|ACTGGCAGCA|GCCACTGGTA|3600|
|ACAGGATTAG|CAGAGCGAGG|TATGTAGGCG|GTGCTACAGA|GTTCTTGAAG|TGGTGGCCTA|3660|
|ACTACGGCTA|CACTAGAAGG|ACAGTATTTG|GTATCTGCGC|TCTGCTGAAG|CCAGTTACCT|3720|
|TCGGAAAAAG|AGTTGGTAGC|TCTTGATCCG|GCAAACAAAC|CACCGCTGGT|AGCGGTGGTT|3780|
|TTTTTGTTTG|CAAGCAGCAG|ATTACGCGCA|GAAAAAAGG|ATCTCAAGAA|GATCCTTTGA|3840|
|TCTTTTCTAC|GGGGTCTGAC|GCTCAGTGGA|ACGAAAACTC|ACGTTAAGGG|ATTTTGGTCA|3900|
|TGAGATTATC|AAAAAGGATC|TTCACCTAGA|TCCTTTTAAA|TTAAAAATGA|AGTTTTAAAT|3960|
|CAATCTAAAG|TATATATGAG|TAAACTTGGT|CTGACAGTTA|CCAATGCTTA|ATCAGTGAGG|4020|
|CACCTATCTC|AGCGATCTGT|CTATTTCGTT|CATCCATAGT|TGCCTGACTC|CCCGTCGTGT|4080|
|AGATAACTAC|GATACGGGAG|GGCTTACCAT|CTGGCCCCAG|TGCTGCAATG|ATACCGCGAG|4140|
|ACCCACGCTC|ACCGGCTCCA|GATTTATCAG|CAATAAACCA|GCCAGCCGGA|AGGGCCGAGC|4200|
|GCAGAAGTGG|TCCTGCAACT|TTATCCGCCT|CCATCCAGTC|TATTAATTGT|TGCCGGGAAG|4260|
|CTAGAGTAAG|TAGTTCGCCA|GTTAATAGTT|TGCGCAACGT|TGTTGCCATT|GCTACAGGCA|4320|
|TCGTGGTGTC|ACGCTCGTCG|TTTGGTATGG|CTTCATTCAG|CTCCGGTTCC|CAACGATCAA|4380|
|GGCGAGTTAC|ATGATCCCCC|ATGTTGTGCA|AAAAAGCGGT|TAGCTCCTTC|GGTCCTCCGA|4440|
|TCGTTGTCAG|AAGTAAGTTG|GCCGCAGTGT|TATCACTCAT|GGTTATGGCA|GCACTGCATA|4500|
|ATTCTCTTAC|TGTCATGCCA|TCCGTAAGAT|GCTTTTCTGT|GACTGGTGAG|TACTCAACCA|4560|
|AGTCATTCTG|AGAATAGTGT|ATGCGGCGAC|CGAGTTGCTC|TTGCCCGGCG|TCAATACGGG|4620|
|ATAATACCGC|GCCACATAGC|AGAACTTTAA|AAGTGCTCAT|CATTGGAAAA|CGTTCTTCGG|4680|
|GGCGAAAACT|CTCAAGGATC|TTACCGCTGT|TGAGATCCAG|TTCGATGTAA|CCCACTCGTG|4740|
|CACCCAACTG|ATCTTCAGCA|TCTTTTACTT|TCACCAGCGT|TTCTGGGTGA|GCAAAAACAG|4800|
|GAAGGCAAAA|TGCCGCAAAA|AAGGGAATAA|GGGCGACACG|GAAATGTTGA|ATACTCATAC|4860|
|TCTTCCTTTT|TCAATATTAT|TGAAGCATTT|ATCAGGGTTA|TTGTCTCATG|AGCGGATACA|4920|
|TATTTGAATG|TATTTAGAAA|AATAAACAAA|TAGGGGTTCC|GCGCACATTT|CCCCGAAAAG|4980|
|TGCCACCTGA|CGTCTAAGAA|ACCATTATTA|TCATGACATT|AACCTATAAA|AATAGGCGTA|5040|
|TCACGAGGCC|CTTTCGTCTC|GCGCGTTTCG|GTGATGACGG|TGAAAACCTC|TGACACATGC|5100|
|AGCTCCCGGA|GACGGTCACA|GCTTGTCTGT|AAGCGGATGC|CGGGAGCAGA|CAAGCCCGTC|5160|
|AGGGCGCGTC|AGCGGGTGTT|GGCGGGTGTC|GGGGCTGGCT|TAACTATGCG|GCATCAGAGC|5220|
|AGATTGTACT|GAGAGTGCAC|CATATGCGGT|GTGAAATACC|GCACAGATGC|GTAAGGAGAA|5280|
|AATACCGCAT|CAGG| | | | |5294|

( 2 ) INFORMATION FOR SEQ ID NO: 3:

( i ) SEQUENCE CHARACTERISTICS:
        ( A ) LENGTH: 5292 base pairs
        ( B ) TYPE: nucleic acid
        ( C ) STRANDEDNESS: double
        ( D ) TOPOLOGY: circular ( i i ) MOLECULE TYPE: DNA ( x i ) SEQUENCE DESCRIPTION: SEQ ID NO: 3:

| | | | | | |
|---|---|---|---|---|---|
| CGATTAGTCC | AATTTGTTAA | AGACAGGATA | TCAGGTGGTC | CAGGCTCTAG | TTTTGACTCA | 60 |
| ACAATATCAC | CAGCTGAAGC | CTATAGAGTA | CGAGCCATAG | ATAGAATAAA | AGATTTTATT | 120 |
| TAGTCTCCAG | AAAAAGGGGG | GAATGAAAGA | CCCCACCTGT | AGGTTTGGCA | AGCTAGCTTA | 180 |
| AGTAACGCCA | TTTTGCAAGG | CATGGAAAAT | ACATAACTGA | GAATAGAGAA | GTTCAGATCA | 240 |
| AGGTTAGGAA | CAGAGAGACA | GCAGAATATG | GGCCAAACAG | GATATCTGTG | GTAAGCAGTT | 300 |
| CCTGCCCCGC | TCAGGGCCAA | GAACAGATGG | TCCCCAGATG | CGGTCCCGCC | CTCAGCAGTT | 360 |
| TCTAGAGAAC | CATCAGATGT | TTCCAGGGTG | CCCCAAGGAC | CTGAAAATGA | CCCTGTGCCT | 420 |
| TATTTGAACT | AACCAATCAG | TTCGCTTCTC | GCTTCTGTTC | GCGCGCTTCT | GCTCCCCGAG | 480 |
| CTCAATAAAA | GAGCCCACAA | CCCCTCACTC | GGCGCGCCAG | TCCTCCGATT | GACTGCGTCG | 540 |
| CCCGGGTACC | GTATTCCCAA | TAAAGCCTCT | TGCTGTTTGC | ATCCGAATCG | TGGTCTCGCT | 600 |
| GTTCCTTGGG | AGGGTCTCCT | CTGAGTGATT | GACTACCCAC | GACGGGGGTC | TTTCATTTGG | 660 |
| GGGCTCGTCC | GGGATTTGGA | GACCCCTGCC | CAGGGACCAC | CGACCCACCA | CCGGGAGGTA | 720 |
| AGCTGGCCAG | CAACTTATCT | GTGTCTGTCC | GATTGTCTAG | TGTCTATGTT | TGATGTTATG | 780 |
| CGCCTGCGTC | TGTACTAGTT | AGCTAACTAG | CTCTGTATCT | GGCGGACCCG | TGGTGGAACT | 840 |
| GACGAGTTCT | GAACACCCGG | CCGCAACCCT | GGGAGACGTC | CCAGGGACTT | GGGGGCCGT | 900 |
| TTTTGTGGCC | CGACCTGAGG | AAGGGAGTCG | ATGTGGAATC | CGACCCCGTC | AGGATATGTG | 960 |
| GTTCTGGTAG | GAGACGAGAA | CCTAAAACAG | TTCCCGCCTC | CGTCTGAATT | TTTGCTTTCG | 1020 |
| GTTTGGAACC | GAAGCCGCGC | GTCTTGTCTG | CTGCAGCATC | GTTCTGTGTT | GTCTCTGTCT | 1080 |
| GACTGTGTTT | CTGTATTTGT | CTGAAAATTA | GGGCCAGACT | GTTACCACTC | CCTTAAGTTT | 1140 |
| GACCTTAGAT | CACTGGAAAG | ATGTCGAGCG | GATCGCTCAC | AACCAGTCGG | TAGATGTCAA | 1200 |
| GAAGAGACGA | TGGGTTACCT | TCTGCTCTGC | AGAATGGCCA | ACCTTTAACG | TCGGATGGCC | 1260 |
| GCGAGACGGC | ACCTTTAACC | GAGACCTCAT | CACCCAGGTT | AAGATCAAGG | TCTTTTCACC | 1320 |
| TGGCCCGCAT | GGACACCCAG | ACCAGGTCCC | CTACATCGTG | ACCTGGGAAG | CCTTGGCTTT | 1380 |
| TGACCCCCCT | CCCTGGGTCA | AGCCCTTTGT | ACACCCTAAG | CCTCCGCCTC | CTCTTCCTCC | 1440 |
| ATCCGCCCCG | TCTCTCCCCC | TTGAACCTCC | TCTTTCGACC | CCGCCTCGAT | CCTCCCTTTA | 1500 |
| TCCAGCCCTC | ACTCCTTCTC | TAGGCGGCTC | CACCGCGGTG | GCGGCCGCTC | TAGAACTAGT | 1560 |
| GGATCCAAGC | TTATCGATAG | GCCTAGGCCT | ATCGATAGGC | CTAGGCCTAT | CGATAGGCCT | 1620 |
| AACACGAGCC | ATAGATAGAA | TAAAGATTT | TATTTAGTCT | CCAGAAAAAG | GGGGAATGA | 1680 |
| AAGACCCCAC | CTGTAGGTTT | GGCAAGCTAG | AGTCGCTTAG | CCTGATAGCC | GCAGTAACGC | 1740 |
| CATTTTGCAA | GGCATGGAAA | AATACCAAAC | CAAGAATAGG | GAAGTTCAGA | TCAAGGGCGG | 1800 |
| GTACATGAAA | ATAGCTAACG | TTGGGCCAAA | CAGGATATCT | GCGGTGAGCA | GTTTCGGCCC | 1860 |
| CGGCCCGGGG | CAAGAACAGA | TGGTCACCGC | AGTTTCGGCC | CCGGCCCGAG | GCCAAGAACA | 1920 |
| GATGGTCCCC | AGATATGGCC | CAACCCTCAG | CAGTTTCTTA | AGACCCATCA | GATGTTTCCA | 1980 |
| GGCTCCCCCA | AGGACCTGAA | ATGACCCTGC | GCCTTATTTG | AATTAACCAA | TCAGCCTGCT | 2040 |
| TCTCGCTTCT | GTTCGCGCGC | TTCTGCTTCC | CGAGCTCTAT | AAAAGAGCTC | ACAACCCCTC | 2100 |
| ACTCGGCGCG | CCAGTCCTCC | GATTGACTGA | GTCGCCCGGG | TACCCGTGTT | CTCAATAAAC | 2160 |
| CCTCTTGCAG | TTGCATCCGA | CTCGTGGTCT | CGCTGTTCCT | TGGGAGGGTC | TCCTCTGAGT | 2220 |
| GATTGACTAC | CCGTCAGCGG | GGGTCTTTCA | GTTCTCCCA | CCTACACAGG | TCTCACTAAC | 2280 |

| | | | | | |
|---|---|---|---|---|---|
| ATTCCTGATG | TGCCGCAGGG | ACTCCGTCAG | CCCGGTTTGT | GTTTATAATA | AAATGCAAGA | 2340 |
| ACAGTGTTCC | CTTCAAGCCA | GACTACATCC | TGACTCTCGG | CTTTATAAAA | GAATGTTGAA | 2400 |
| GGGCTCTGTG | GACTATCTGC | CACACGACTT | TTAAGATTTT | TATGCCTCCT | GGATGAGGGA | 2460 |
| TTTAGTCAAT | CTATCCTCGT | CTATTTTGCT | GGCTTCTCCG | TATTTTAAAT | TTCTAGTTTG | 2520 |
| CACTCCCTTC | CTGAGAGCAC | GGCGATTGCA | GAGTAGTTAA | TACTCTGAGG | GCAGGCTTCT | 2580 |
| GTGAAAAGGT | TGCCTGGGCT | CAGTGTGAGA | TTTTGCCATA | AAAGGGGTC | CTGCCCCTGT | 2640 |
| GTACAGACAG | ATCGGAATCT | AGAGTGCATA | CTCAGAGTCC | CCGCGGTTCC | GGGGCTCTGA | 2700 |
| TCTCAGGGCA | TCTTTGCCTA | GAGATCCTCT | ACGCCGGACG | CATCGTGGCC | GGCATCACCG | 2760 |
| GCGCCACAGG | TGCGGTTGCT | GGCGCCTATA | TCGCCGACAT | CACCGATGGG | GAAGATCGGG | 2820 |
| CTCGCCACTT | CGGGCTCATG | AGCGCTTGTT | TCGGCGTGGG | TATGGTGGCA | GGCCCCGTGG | 2880 |
| CCGGGGGACT | GTTGGGCGCC | ATCTCCTTGC | ATGCACCATT | CCTTGCGGCG | GCGGTGCTCA | 2940 |
| ACGGCCTCAA | CCTACTACTG | GGCTGCTTCC | TAATGCAGGA | GTCGCATAAG | GGAGAGCGTC | 3000 |
| CTGCATTAAT | GAATCGGCCA | ACGCGCGGGG | AGAGGCGGTT | TGCGTATTGG | GCGCTCTTCC | 3060 |
| GCTTCCTCGC | TCACTGACTC | GCTGCGCTCG | GTCGTTCGGC | TGCGGCGAGC | GGTATCAGCT | 3120 |
| CACTCAAAGG | CGGTAATACG | GTTATCCACA | GAATCAGGGG | ATAACGCAGG | AAAGAACATG | 3180 |
| TGAGCAAAAG | GCCAGCAAAA | GGCCAGGAAC | CGTAAAAAGG | CCGCGTTGCT | GGCGTTTTTC | 3240 |
| CATAGGCTCC | GCCCCCCTGA | CGAGCATCAC | AAAAATCGAC | GCTCAAGTCA | GAGGTGGCGA | 3300 |
| AACCCGACAG | GACTATAAAG | ATACCAGGCG | TTTCCCCCTG | GAAGCTCCCT | CGTGCGCTCT | 3360 |
| CCTGTTCCGA | CCCTGCCGCT | TACCGGATAC | CTGTCCGCCT | TTCTCCCTTC | GGGAAGCGTG | 3420 |
| GCGCTTTCTC | AATGCTCACG | CTGTAGGTAT | CTCAGTTCGG | TGTAGGTCGT | TCGCTCCAAG | 3480 |
| CTGGGCTGTG | TGCACGAACC | CCCCGTTCAG | CCCGACCGCT | GCGCCTTATC | CGGTAACTAT | 3540 |
| CGTCTTGAGT | CCAACCCGGT | AAGACACGAC | TTATCGCCAC | TGGCAGCAGC | CACTGGTAAC | 3600 |
| AGGATTAGCA | GAGCGAGGTA | TGTAGGCGGT | GCTACAGAGT | TCTTGAAGTG | GTGGCCTAAC | 3660 |
| TACGGCTACA | CTAGAAGGAC | AGTATTTGGT | ATCTGCGCTC | TGCTGAAGCC | AGTTACCTTC | 3720 |
| GGAAAAAGAG | TTGGTAGCTC | TTGATCCGGC | AAACAAACCA | CCGCTGGTAG | CGGTGGTTTT | 3780 |
| TTTGTTTGCA | AGCAGCAGAT | TACGCGCAGA | AAAAAAGGAT | CTCAAGAAGA | TCCTTTGATC | 3840 |
| TTTTCTACGG | GGTCTGACGC | TCAGTGGAAC | GAAAACTCAC | GTTAAGGGAT | TTTGGTCATG | 3900 |
| AGATTATCAA | AAAGGATCTT | CACCTAGATC | CTTTTAAATT | AAAAATGAAG | TTTTAAATCA | 3960 |
| ATCTAAAGTA | TATATGAGTA | AACTTGGTCT | GACAGTTACC | AATGCTTAAT | CAGTGAGGCA | 4020 |
| CCTATCTCAG | CGATCTGTCT | ATTTCGTTCA | TCCATAGTTG | CCTGACTCCC | CGTCGTGTAG | 4080 |
| ATAACTACGA | TACGGGAGGG | CTTACCATCT | GGCCCCAGTG | CTGCAATGAT | ACCGCGAGAC | 4140 |
| CCACGCTCAC | CGGCTCCAGA | TTTATCAGCA | ATAAACCAGC | CAGCCGGAAG | GGCCGAGCGC | 4200 |
| AGAAGTGGTC | CTGCAACTTT | ATCCGCCTCC | ATCCAGTCTA | TTAATTGTTG | CCGGGAAGCT | 4260 |
| AGAGTAAGTA | GTTCGCCAGT | TAATAGTTTG | CGCAACGTTG | TTGCCATTGC | TACAGGCATC | 4320 |
| GTGGTGTCAC | GCTCGTCGTT | TGGTATGGCT | TCATTCAGCT | CCGGTTCCCA | ACGATCAAGG | 4380 |
| CGAGTTACAT | GATCCCCCAT | GTTGTGCAAA | AAAGCGGTTA | GCTCCTTCGG | TCCTCCGATC | 4440 |
| GTTGTCAGAA | GTAAGTTGGC | CGCAGTGTTA | TCACTCATGG | TTATGGCAGC | ACTGCATAAT | 4500 |
| TCTCTTACTG | TCATGCCATC | CGTAAGATGC | TTTTCTGTGA | CTGGTGAGTA | CTCAACCAAG | 4560 |
| TCATTCTGAG | AATAGTGTAT | GCGGCGACCG | AGTTGCTCTT | GCCCGGCGTC | AATACGGGAT | 4620 |
| AATACCGCGC | CACATAGCAG | AACTTTAAAA | GTGCTCATCA | TTGGAAAACG | TTCTTCGGGG | 4680 |

```
CGAAAACTCT  CAAGGATCTT  ACCGCTGTTG  AGATCCAGTT  CGATGTAACC  CACTCGTGCA    4740
CCCAACTGAT  CTTCAGCATC  TTTTACTTTC  ACCAGCGTTT  CTGGGTGAGC  AAAAACAGGA    4800
AGGCAAAATG  CCGCAAAAAA  GGGAATAAGG  GCGACACGGA  AATGTTGAAT  ACTCATACTC    4860
TTCCTTTTTC  AATATTATTG  AAGCATTTAT  CAGGGTTATT  GTCTCATGAG  CGGATACATA    4920
TTTGAATGTA  TTTAGAAAAA  TAAACAAATA  GGGGTTCCGC  GCACATTTCC  CCGAAAAGTG    4980
CCACCTGACG  TCTAAGAAAC  CATTATTATC  ATGACATTAA  CCTATAAAAA  TAGGCGTATC    5040
ACGAGGCCCT  TTCGTCTCGC  GCGTTTCGGT  GATGACGGTG  AAAACCTCTG  ACACATGCAG    5100
CTCCCGGAGA  CGGTCACAGC  TTGTCTGTAA  GCGGATGCCG  GGAGCAGACA  AGCCCGTCAG    5160
GGCGCGTCAG  CGGGTGTTGG  CGGGTGTCGG  GGCTGGCTTA  ACTATGCGGC  ATCAGAGCAG    5220
ATTGTACTGA  GAGTGCACCA  TATGCGGTGT  GAAATACCGC  ACAGATGCGT  AAGGAGAAAA    5280
TACCGCATCA  GG                                                            5292
```

( 2 ) INFORMATION FOR SEQ ID NO: 4:

( i ) SEQUENCE CHARACTERISTICS:
        ( A ) LENGTH: 5364 base pairs
        ( B ) TYPE: nucleic acid
        ( C ) STRANDEDNESS: double
        ( D ) TOPOLOGY: circular ( i i ) MOLECULE TYPE: DNA ( x i ) SEQUENCE DESCRIPTION: SEQ ID NO: 4:

```
CGATTAGTCC  AATTTGTTAA  AGACAGGATA  TCAGGTGGTC  CAGGCTCTAG  TTTTGACTCA      60
ACAATATCAC  CAGCTGAAGC  CTATAGAGTA  CGAGCCATAG  ATAGAATAAA  AGATTTTATT     120
TAGTCTCCAG  AAAAAGGGGG  GAATGAAAGA  CCCCACCTGT  AGGTTTGGCA  AGCTAGCTTA     180
AGTAACGCCA  TTTTGCAAGG  CATGGAAAAT  ACATAACTGA  GAATAGAGAA  GTTCAGATCA     240
AGGTTAGGAA  CAGAGAGACA  GCAGAATATG  GGCCAAACAG  GATATCTGTG  GTAAGCAGTT     300
CCTGCCCCGC  TCAGGGCCAA  GAACAGATGG  TCCCCAGATG  CGGTCCCGCC  CTCAGCAGTT     360
TCTAGAGAAC  CATCAGATGT  TTCCAGGGTG  CCCCAAGGAC  CTGAAAATGA  CCCTGTGCCT     420
TATTTGAACT  AACCAATCAG  TTCGCTTCTC  GCTTCTGTTC  GCGCGCTTCT  GCTCCCCGAG     480
CTCAATAAAA  GAGCCCACAA  CCCCTCACTC  GGCGCGCCAG  TCCTCCGATT  GACTGCGTCG     540
CCCGGGTACC  CGTATTCCCA  ATAAAGCCTC  TTGCTGTTTG  CATCCGAATC  GTGGACTCGC     600
TGATCCTTGG  GAGGGTCTCC  TCAGATTGAT  TGACTGCCCA  CCTCGGGGGT  CTTTCATTTG     660
GAGGTTCCAC  CGAGATTTGG  AGACCCCAGC  CCAGGGACCA  CCGACCCCCC  CGCCGGGAGG     720
TAAGCTGGCC  AGCGGTCGTT  TCGTGTCTGT  CTCTGTCTTT  GTGCGTGTTT  GTGCCGGCAT     780
CTAATGTTTG  CGCCTGCGTC  TGTACTAGTT  GGCTAACTAG  ATCTGTATCT  GGCGGTCCCG     840
CGGAAGAACT  GACGAGTTCG  TATTCCCGGC  CGCAGCCCCT  AGGAGACGTC  CAGCGGCCT      900
CGGGGGCCCG  TTTTGTGGCC  CGTTCTGTGT  CGTTAACCAC  CCGAGTCGGA  CTTTTGGAG      960
CTCCGCCACT  GTCCGAGGGG  TACGTGGCTT  TGTTGGGGGA  CGAGAGACAG  AGACACTTCC    1020
CGCCCCCGTC  TGAATTTTTG  CTTTCGGTTT  TACGCCGAAA  CCGCGCCGCG  CGTCTTGTCT    1080
GCTGCAGCAT  CGTTCTGTGT  TGTCTCTGTC  TGACTGTGTT  TCTGTATTTG  TCTGAAAATT    1140
AGGGCCAGAC  TGTTACCACT  CCCTTAAGTT  TGACCTTAGA  TCACTGGAAA  GATGTCGAGC    1200
GGATCGCTCA  CAACCAGTCG  GTAGATGTCA  AGAAGAGACG  ATGGGTTACC  TTCTGCTCTG    1260
CAGAATGGCC  AACCTTTAAC  GTCGGATGGC  CGCGAGACGG  CACCTTTAAC  CGAGACCTCA    1320
```

| | | | | | | |
|---|---|---|---|---|---|---|
| TCACCCAGGT | TAAGATCAAG | GTCTTTTCAC | CTGGCCCGCA | TGGACACCCA | GACCAGGTCC | 1380 |
| CCTACATCGT | GACCTGGGAA | GCCTTGGCTT | TTGACCCCCC | TCCCTGGGTC | AAGCCCTTTG | 1440 |
| TACACCCTAA | GCCTCCGCCT | CCTCTTCCTC | CATCCGCCCC | GTCTCTCCCC | CTTGAACCTC | 1500 |
| CTCTTTCGAC | CCCGCCTCGA | TCCTCCCTTT | ATCCAGCCCT | CACTCCTTCT | CTAGGCGGCT | 1560 |
| CCACCGCGGT | GGCGGCCGCT | CTAGAACTAG | TGGATCCAAG | CTTATCGATA | GGCCTAGGCC | 1620 |
| TATCGATAGG | CCTAGGCCTA | TCGATAGGCC | TAACACGAGC | CATAGATAGA | ATAAAGATT | 1680 |
| TTATTTAGTC | TCCAGAAAAA | GGGGGGAATG | AAAGACCCCA | CCTGTAGGTT | TGGCAAGCTA | 1740 |
| GAGTCGCTTA | GCCTGATAGC | CGCAGTAACG | CCATTTTGCA | AGGCATGGAA | AAATACCAAA | 1800 |
| CCAAGAATAG | GGAAGTTCAG | ATCAAGGGCG | GGTACATGAA | AATAGCTAAC | GTTGGGCCAA | 1860 |
| ACAGGATATC | TGCGGTGAGC | AGTTTCGGCC | CCGGCCCGGG | GCAAGAACAG | ATGGTCACCG | 1920 |
| CAGTTTCGGC | CCCGGCCCGG | GCCAAGAACA | GATGGTCACC | GCAGTTTCGG | CCCCGGCCCG | 1980 |
| GGGCCAAGAA | CAGATGGTCC | CCAGATATGG | CCCAACCCTC | AGCAGTTTCT | TAAGACCCAT | 2040 |
| CAGATGTTTC | CAGGCTCCCC | CAAGGACCTG | AAATGACCCT | GCGCCTTATT | TGAATTAACC | 2100 |
| AATCAGCCTG | CTTCTCGCTT | CTGTTCGCGC | GCTTCTGCTT | CCCGAGCTCT | ATAAAAGAGC | 2160 |
| TCACAACCCC | TCACTCGGCG | CGCCAGTCCT | CCGATTGACT | GAGTCGCCCG | GGTACCCGTG | 2220 |
| TTCTCAATAA | ACCCTCTTGC | AGTTGCATCC | GACTCGTGGT | CTCGCTGTTC | CTTGGGAGGG | 2280 |
| TCTCCTCTGA | GTGATTGACT | ACCCGTCAGC | GGGGGTCTTT | CAGTTTCTCC | CACCTACACA | 2340 |
| GGTCTCACTA | ACATTCCTGA | TGTGCCGCAG | GGACTCCGTC | AGCCCGGTTT | GTGTTTATAA | 2400 |
| TAAAATGCAA | GAACAGTGTT | CCCTTCAAGC | CAGACTACAT | CCTGACTCTC | GGCTTTATAA | 2460 |
| AAGAATGTTG | AAGGGCTCTG | TGGACTATCT | GCCACACGAC | TTTTAAGATT | TTTATGCCTC | 2520 |
| CTGGATGAGG | GATTTAGTCA | ATCTATCCTC | GTCTATTTTG | CTGGCTTCTC | CGTATTTTAA | 2580 |
| ATTTCTAGTT | TGCACTCCCT | TCCTGAGAGC | ACGGCGATTG | CAGAGTAGTT | AATACTCTGA | 2640 |
| GGGCAGGCTT | CTGTGAAAAG | GTTGCCTGGG | CTCAGTGTGA | GATTTTGCCA | TAAAAGGGG | 2700 |
| TCCTGCCCCT | GTGTACAGAC | AGATCGGAAT | CTAGAGTGCA | TACTCAGAGT | CCCCGCGGTT | 2760 |
| CCGGGGCTCT | GATCTCAGGG | CATCTTTGCC | TAGAGATCCT | CTACGCCGGA | CGCATCGTGG | 2820 |
| CCGGCATCAC | CGGCGCCACA | GGTGCGGTTG | CTGGCGCCTA | TATCGCCGAC | ATCACCGATG | 2880 |
| GGGAAGATCG | GGCTCGCCAC | TTCGGGCTCA | TGAGCGCTTG | TTTCGGCGTG | GGTATGGTGG | 2940 |
| CAGGCCCCGT | GGCCGGGGGA | CTGTTGGGCG | CCATCTCCTT | GCATGCACCA | TTCCTTGCGG | 3000 |
| CGGCGGTGCT | CAACGGCCTC | AACCTACTAC | TGGGCTGCTT | CCTAATGCAG | GAGTCGCATA | 3060 |
| AGGGAGAGCG | TCCTGCATTA | ATGAATCGGC | CAACGCGCGG | GGAGAGGCGG | TTTGCGTATT | 3120 |
| GGGCGCTCTT | CCGCTTCCTC | GCTCACTGAC | TCGCTGCGCT | CGGTCGTTCG | GCTGCGGCGA | 3180 |
| GCGGTATCAG | CTCACTCAAA | GGCGGTAATA | CGGTTATCCA | CAGAATCAGG | GGATAACGCA | 3240 |
| GGAAAGAACA | TGTGAGCAAA | AGGCCAGCAA | AAGGCCAGGA | ACCGTAAAAA | GGCCGCGTTG | 3300 |
| CTGGCGTTTT | TCCATAGGCT | CCGCCCCCCT | GACGAGCATC | ACAAAAATCG | ACGCTCAAGT | 3360 |
| CAGAGGTGGC | GAAACCCGAC | AGGACTATAA | AGATACCAGG | CGTTTCCCCC | TGGAAGCTCC | 3420 |
| CTCGTGCGCT | CTCCTGTTCC | GACCCTGCCG | CTTACCGGAT | ACCTGTCCGC | CTTTCTCCCT | 3480 |
| TCGGGAAGCG | TGGCGCTTTC | TCAATGCTCA | CGCTGTAGGT | ATCTCAGTTC | GGTGTAGGTC | 3540 |
| GTTCGCTCCA | AGCTGGGCTG | TGTGCACGAA | CCCCCCGTTC | AGCCCGACCG | CTGCGCCTTA | 3600 |
| TCCGGTAACT | ATCGTCTTGA | GTCCAACCCG | GTAAGACACG | ACTTATCGCC | ACTGGCAGCA | 3660 |
| GCCACTGGTA | ACAGGATTAG | CAGAGCGAGG | TATGTAGGCG | GTGCTACAGA | GTTCTTGAAG | 3720 |

| | | | | | | |
|---|---|---|---|---|---|---|
| TGGTGGCCTA | ACTACGGCTA | CACTAGAAGG | ACAGTATTTG | GTATCTGCGC | TCTGCTGAAG | 3780 |
| CCAGTTACCT | TCGGAAAAAG | AGTTGGTAGC | TCTTGATCCG | GCAAACAAAC | CACCGCTGGT | 3840 |
| AGCGGTGGTT | TTTTTGTTTG | CAAGCAGCAG | ATTACGCGCA | GAAAAAAGG | ATCTCAAGAA | 3900 |
| GATCCTTTGA | TCTTTTCTAC | GGGGTCTGAC | GCTCAGTGGA | ACGAAAACTC | ACGTTAAGGG | 3960 |
| ATTTTGGTCA | TGAGATTATC | AAAAAGGATC | TTCACCTAGA | TCCTTTTAAA | TTAAAAATGA | 4020 |
| AGTTTTAAAT | CAATCTAAAG | TATATATGAG | TAAACTTGGT | CTGACAGTTA | CCAATGCTTA | 4080 |
| ATCAGTGAGG | CACCTATCTC | AGCGATCTGT | CTATTTCGTT | CATCCATAGT | TGCCTGACTC | 4140 |
| CCCGTCGTGT | AGATAACTAC | GATACGGGAG | GGCTTACCAT | CTGGCCCCAG | TGCTGCAATG | 4200 |
| ATACCGCGAG | ACCCACGCTC | ACCGGCTCCA | GATTTATCAG | CAATAAACCA | GCCAGCCGGA | 4260 |
| AGGGCCGAGC | GCAGAAGTGG | TCCTGCAACT | TTATCCGCCT | CCATCCAGTC | TATTAATTGT | 4320 |
| TGCCGGGAAG | CTAGAGTAAG | TAGTTCGCCA | GTTAATAGTT | TGCGCAACGT | TGTTGCCATT | 4380 |
| GCTACAGGCA | TCGTGGTGTC | ACGCTCGTCG | TTTGGTATGG | CTTCATTCAG | CTCCGGTTCC | 4440 |
| CAACGATCAA | GGCGAGTTAC | ATGATCCCCC | ATGTTGTGCA | AAAAAGCGGT | TAGCTCCTTC | 4500 |
| GGTCCTCCGA | TCGTTGTCAG | AAGTAAGTTG | GCCGCAGTGT | TATCACTCAT | GGTTATGGCA | 4560 |
| GCACTGCATA | ATTCTCTTAC | TGTCATGCCA | TCCGTAAGAT | GCTTTTCTGT | GACTGGTGAG | 4620 |
| TACTCAACCA | AGTCATTCTG | AGAATAGTGT | ATGCGGCGAC | CGAGTTGCTC | TTGCCCGGCG | 4680 |
| TCAATACGGG | ATAATACCGC | GCCACATAGC | AGAACTTTAA | AAGTGCTCAT | CATTGGAAAA | 4740 |
| CGTTCTTCGG | GGCGAAAACT | CTCAAGGATC | TTACCGCTGT | TGAGATCCAG | TTCGATGTAA | 4800 |
| CCCACTCGTG | CACCCAACTG | ATCTTCAGCA | TCTTTTACTT | TCACCAGCGT | TTCTGGGTGA | 4860 |
| GCAAAAACAG | GAAGGCAAAA | TGCCGCAAAA | AAGGGAATAA | GGGCGACACG | GAAATGTTGA | 4920 |
| ATACTCATAC | TCTTCCTTTT | TCAATATTAT | TGAAGCATTT | ATCAGGGTTA | TTGTCTCATG | 4980 |
| AGCGGATACA | TATTTGAATG | TATTTAGAAA | AATAAACAAA | TAGGGGTTCC | GCGCACATTT | 5040 |
| CCCCGAAAAG | TGCCACCTGA | CGTCTAAGAA | ACCATTATTA | TCATGACATT | AACCTATAAA | 5100 |
| AATAGGCGTA | TCACGAGGCC | CTTTCGTCTC | GCGCGTTTCG | GTGATGACGG | TGAAAACCTC | 5160 |
| TGACACATGC | AGCTCCCGGA | GACGGTCACA | GCTTGTCTGT | AAGCGGATGC | CGGGAGCAGA | 5220 |
| CAAGCCCGTC | AGGGCGCGTC | AGCGGGTGTT | GGCGGGTGTC | GGGGCTGGCT | TAACTATGCG | 5280 |
| GCATCAGAGC | AGATTGTACT | GAGAGTGCAC | CATATGCGGT | GTGAAATACC | GCACAGATGC | 5340 |
| GTAAGGAGAA | AATACCGCAT | CAGG | | | | 5364 |

(2) INFORMATION FOR SEQ ID NO: 5:

(i) SEQUENCE CHARACTERISTICS:
        (A) LENGTH: 6505 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO: 5:

| | | | | | | |
|---|---|---|---|---|---|---|
| TCGAGGGGGG | GCCCGGTACC | GATTAGTCCA | ATTTGTTAAA | GACAGGATAT | CAGGTGGTCC | 60 |
| AGGCTCTAGT | TTTGACTCAA | CAATATCACC | AGCTGAAGCC | TATAGAGTAC | GAGCCATAGA | 120 |
| TAGAATAAAA | GATTTTATTT | AGTCTCCAGA | AAAAGGGGGG | AATGAAAGAC | CCCACCTGTA | 180 |
| GGTTTGGCAA | GCTAGCTTAA | GTAACGCCAT | TTTGCAAGGC | ATGGAAAATA | CATAACTGAG | 240 |
| AATAGAGAAG | TTCAGATCAA | GGTTAGGAAC | AGAGAGACAG | CAGAATATGG | GCCAAACAGG | 300 |
| ATATCTGTGG | TAAGCAGTTC | CTGCCCCGCT | CAGGGCCAAG | AACAGATGGT | CCCCAGATGC | 360 |

```
GGTCCCGCCC TCAGCAGTTT CTAGAGAACC ATCAGATGTT TCCAGGGTGC CCCAAGGACC    420
TGAAAATGAC CCTGTGCCTT ATTTGAACTA ACCAATCAGT TCGCTTCTCG CTTCTGTTCG    480
CGCGCTTCTG CTCCCCGAGC TCAATAAAAG AGCCCACAAC CCCTCACTCG GCGCGCCAGT    540
CCTCCGATTG ACTGCGTCGC CCGGGTACCC GTATTCCCAA TAAAGCCTCT TGCTGTTTGC    600
ATCCGAATCG TGGACTCGCT GATCCTTGGG AGGGTCTCCT CAGATTGATT GACTGCCCAC    660
CTCGGGGGTC TTTCATTTGG AGGTTCCACC GAGATTTGGA GACCCCAGCC CAGGGACCAC    720
CGACCCCCCC GCCGGGAGGT AAGCTGGCCA GCGGTCGTTT CGTGTCTGTC TCTGTCTTTG    780
TGCGTGTTTG TGCCGGCATC TAATGTTTGC GCCTGCGTCT GTACTAGTTG GCTAACTAGA    840
TCTGTATCTG GCGGTCCCGC GGAAGAACTG ACGAGTTCGT ATTCCCGGCC GCAGCCCCTA    900
GGAGACGTCC CAGCGGCCTC GGGGGCCCGT TTTGTGGCCC GTTCTGTGTC GTTAACCACC    960
CGAGTCGGAC TTTTTGGAGC TCCGCCACTG TCCGAGGGGT ACGTGGCTTT GTTGGGGGAC   1020
GAGAGACAGA GACACTTCCC GCCCCCGTCT GAATTTTTGC TTTCGGTTTT ACGCCGAAAC   1080
CGCGCCGCGC GTCTTGTCTG CTGCAGCATC GTTCTGTGTT GTCTCTGTCT GACTGTGTTT   1140
CTGTATTTGT CTGAAAATTA GGGCCAGACT GTTACCACTC CCTTAAGTTT GACCTTAGAT   1200
CACTGGAAAG ATGTCGAGCG GATCGCTCAC AACCAGTCGG TAGATGTCAA GAAGAGACGA   1260
TGGGTTACCT TCTGCTCTGC AGAATGGCCA ACCTTTAACG TCGGATGGCC GCGAGACGGC   1320
ACCTTTAACC GAGACCTCAT CACCCAGGTT AAGATCAAGG TCTTTTCACC TGGCCCGCAT   1380
GGACACCCAG ACCAGGTCCC CTACATCGTG ACCTGGGAAG CCTTGGCTTT TGACCCCCCT   1440
CCCTGGGTCA AGCCCTTTGT ACACCCTAAG CCTCCGCCTC CTCTTCCTCC ATCCGCCCCG   1500
TCTCTCCCCC TTGAACCTCC TCTTTCGACC CCGCCTCGAT CCTCCCTTTA TCCAGCCCTC   1560
ACTCCTTCTC TAGGCGGCTC CACCGCGGTG GCGGCCGATC CCCCGGGCTG CAGGAATTCG   1620
ATATCAAGCT TATCGATACC GTCGACTCTA GAGGATCCCG CCGCGGCGGG TACCGAGCTC   1680
ATTCGAGTAG CGGCTCTTCC AAGCTCAAAG AAGCAGAGGC CGCTGTTCGT TCCTTTAGG    1740
TCTTTCCACT AAAGTCGGAG TATCTTCTTC CAAGATTTCA CGTCTTGGTG GCCGTTCCAA   1800
GGAGCGCGAG GTCGGGATGG ATCTTGAAGG GGACCGCAAT GGAGGAGCAA AGAAGAAGAA   1860
CTTTTTTAAA CTGAACAATA AAAGTGAAAA AGATAAGAAG GAAAAGAAAC CAACTGTCAG   1920
TGTATTTTCA ATGTTTCGCT ATTCAAATTG GCTTGACAAG TTGTATATGG TGGTGGGAAC   1980
TTTGGCTGCC ATCATCCATG GGCTGGACT TCCTCTCATG ATGCTGGTGT TTGGAGAAAT    2040
GACAGATATC TTTGCAAATG CAGGAAATTT AGAAGATCTG ATGTCAAACA TCACTAATAG   2100
AAGTGATATC AATGATACAG GGTTCTTCAT GAATCTGGAG GAAGACATGA CCAGGTATGC   2160
CTATTATTAC AGTGGAATTG GTGCTGGGGT GCTGGTTGCT GCTTACATTC AGGTTTCATT   2220
TTGGTGCCTG GCAGCTGGAA GACAAATACA CAAAATTAGA AACAGTTTT TCATGCTAT    2280
AATGCGACAG GAGATAGGCT GGTTTGATGT GCACGATGTT GGGGAGCTTA ACACCCGACT   2340
TACAGATGAT GTCTCTAAGA TTAATGAAGT TATTGGTGAC AAAATTGGAA TGTTCTTTCA   2400
GTCAATGGCA ACATTTTTCA CTGGGTTTAT AGTAGGATTT ACACGTGGTT GGAAGCTAAC   2460
CCTTGTGATT TTGGCCATCA GTCCTGTTCT TGGACTGTCA GCTGCTGTCT GGGCAAAGAT   2520
ACTATCTTCA TTTACTGATA AAGAACTCTT AGCGTATGCA AAAGCTGGAG CAGTAGCTGA   2580
AGAGGTCTTG GCAGCAATTA GAACTGTGAT TGCATTTGGA GGACAAAAGA AGAACTTGA    2640
AAGGTACAAC AAAAATTTAG AAGAAGCTAA AAGAATTGGG ATAAAGAAAG CTATTACAGC   2700
CAATATTTCT ATAGGTGCTG CTTTCCTGCT GATCTATGCA TCTTATGCTC TGGCCTTCTG   2760
```

```
GTATGGGACC ACCTTGGTCC TCTCAGGGGA ATATTCTATT GGACAAGTAC TCACTGTATT    2820
CTTTTCTGTA TTAATTGGGG CTTTTAGTGT TGGACAGGCA TCTCCAAGCA TTGAAGCATT    2880
TGCAAATGCA AGAGGAGCAG CTTATGAAAT CTTCAAGATA ATTGATAATA AGCCAAGTAT    2940
TGACAGCTAT TCGAAGAGTG GGCACAAACC AGATAATATT AAGGGAAATT TGGAATTCAG    3000
AAATGTTCAC TTCAGTTACC CATCTCGAAA AGAAGTTAAG ATCTTGAAGG GCCTGAACCT    3060
GAAGGTGCAG AGTGGGCAGA CGGTGGCCCT GGTTGGAAAC AGTGGCTGTG GAAGAGCAC    3120
AACAGTCCAG CTGATGCAGA GGCTCTATGA CCCCACAGAG GGATGGTCA GTGTTGATGG    3180
ACAGGATATT AGGACCATAA ATGTAAGGTT TCTACGGGAA ATCATTGGTG TGGTGAGTCA    3240
GGAACCTGTA TTGTTTGCCA CCACGATAGC TGAAACATT CGCTATGGCC GTGAAAATGT    3300
CACCATGGAT GAGATTGAGA AAGCTGTCAA GGAAGCCAAT GCCTATGACT TATCATGAA    3360
ACTGCCTCAT AAATTTGACA CCCTGGTTGG AGAGAGAGGG GCCCAGTTGA GTGGTGGGCA    3420
GAAGCAGAGG ATCGCCATTG CACGTGCCCT GGTTCGCAAC CCCAAGATCC TCCTGCTGGA    3480
TGAGGCCACG TCAGCCTTGG ACACAGAAAG CGAAGCAGTG GTTCAGGTGG CTCTGGATAA    3540
GGCCAGAAAA GGTCGGACCA CCATTGTGAT AGCTCATCGT TTGTCTACAG TTCGTAATGC    3600
TGACGTCATC GCTGGTTTCG ATGATGGAGT CATTGTGGAG AAAGGAAATC ATGATGAACT    3660
CATGAAAGAG AAAGGCATTT ACTTCAAACT TGTCACAATG CAGACAGCAG GAAATGAAGT    3720
TGAATTAGAA AATGCAGCTG ATGAATCCAA AAGTGAAATT GATGCCTTGG AAATGTCTTC    3780
AAATGATTCA AGATCCAGTC TAATAAGAAA AAGATCAACT CGTAGGAGTG TCCGTGGATC    3840
ACAAGCCCAA GACAGAAAGC TTAGTACCAA AGAGGCTCTG GATGAAAGTA TACCTCCAGT    3900
TTCCTTTTGG AGGATTATGA AGCTAAATTT AACTGAATGG CCTTATTTTG TTGTTGGTGT    3960
ATTTTGTGCC ATTATAAATG GAGGCCTGCA ACCAGCATTT GCAATAATAT TTCAAAGAT    4020
TATAGGGGTT TTTACAAGAA TTGATGATCC TGAAACAAAA CGACAGAATA GTAACTTGTT    4080
TTCACTATTG TTTCTAGCCC TTGGAATTAT TTCTTTTATT ACATTTTTCC TTCAGGGTTT    4140
CACATTTGGC AAAGCTGGAG AGATCCTCAC CAAGCGGCTC CGATACATGG TTTTCCGATC    4200
CATGCTCAGA CAGGATGTGA GTTGGTTTGA TGACCCTAAA AACACCACTG GAGCATTGAC    4260
TACCAGGCTC GCCAATGATG CTGCTCAAGT TAAAGGGGCT ATAGGTTCCA GGCTTGCTGT    4320
AATTACCCAG AATATAGCAA ATCTTGGGAC AGGAATAATT ATATCCTTCA TCTATGGTTG    4380
GCAACTAACA CTGTTACTCT TAGCAATTGT ACCCATCATT GCAATAGCAG GAGTTGTTGA    4440
AATGAAAATG TTGTCTGGAC AAGCACTGAA AGATAAGAAA GAACTAGAAG GTGCTGGGAA    4500
GATCGCTACT GAAGCAATAG AAAACTTCCG AACCGTTGTT TCTTTGACTC AGGAGCAGAA    4560
GTTTGAACAT ATGTATGCTC AGAGTTTGCA GGTACCATAC AGAAACTCTT TGAGGAAAGC    4620
ACACATCTTT GGAATTACAT TTTCCTTCAC CCAGGCAATG ATGTATTTTT CCTATGCTGG    4680
ATGTTTCCGG TTTGGAGCCT ACTTGGTGGC ACATAAACTC ATGAGCTTTG AGGATGTTCT    4740
GTTAGTATTT TCAGCTGTTG TCTTTGGTGC CATGGCCGTG GGGCAAGTCA GTTCATTTGC    4800
TCCTGACTAT GCCAAAGCCA AAATATCAGC AGCCCACATC ATCATGATCA TTGAAAAAAC    4860
CCCTTTGATT GACAGCTACA GCACGGAAGG CCTAATGCCG AACACATTGG AAGGAAATGT    4920
CACATTTGGT GAAGTTGTAT TCAACTATCC CACCCGACCG GACATCCCAG TGCTTCAGGG    4980
ACTGAGCCTG GAGGTGAAGA AGGGCCAGAC GCTGGCTCTG GTGGGCAGCA GTGGCTGTGG    5040
GAAGAGCACA GTGGTCCAGC TCCTGGAGCG GTTCTACGAC CCCTTGGCAG GGAAAGTGCT    5100
GCTTGATGGC AAAGAAATAA AGCGACTGAA TGTTCAGTGG CTCCGAGCAC ACCTGGGCAT    5160
```

| | | | | | |
|---|---|---|---|---|---|
|CGTGTCCCAG|GAGCCCATCC|TGTTTGACTG|CAGCATTGCT|GAGAACATTG|CCTATGGAGA 5220|
|CAACAGCCGG|GTGGTGTCAC|AGGAAGAGAT|CGTGAGGGCA|GCAAGGAGG|CCAACATACA 5280|
|TGCCTTCATC|GAGTCACTGC|CTAATAAATA|TAGCACTAAA|GTAGGAGACA|AAGGAACTCA 5340|
|GCTCTCTGGT|GGCCAGAAAC|AACGCATTGC|CATAGCTCGT|GCCCTTGTTA|GACAGCCTCA 5400|
|TATTTGCTT|TTGGATGAAG|CCACGTCAGC|TCTGGATACA|GAAAGTGAAA|AGGTTGTCCA 5460|
|AGAAGCCCTG|GACAAAGCCA|GAGAAGGCCG|CACCTGCATT|GTGATTGCTC|ACCGCCTGTC 5520|
|CACCATCCAG|AATGCAGACT|TAATAGTGGT|GTTTCAGAAT|GGCAGAGTCA|AGGAGCATGG 5580|
|CACGCATCAG|CAGCTGCTGG|CACAGAAAGG|CATCTATTTT|TCAATGGTCA|GTGTCCAGGC 5640|
|TGGAACAAAG|CGCCAGTGAA|CTCTGACTGT|ATGAGATGTT|AAATACTTTT|TAATGGGATC 5700|
|CACTAGTTCT|AGAGCGGCCG|CCACCGCGGT|GGAGCTATCC|ACCATCATGG|GGCTTCTCAT 5760|
|TATACTCCTA|CTCCTACTAA|TTCTGCTTTT|GTGGACCCTG|CATTCTTAAT|CGATTAGTTC 5820|
|AATTTGTTAA|AGACAGGATC|TCAGTAGTCC|AGGCTTTAGT|CCTGACTCAA|CAATACCACC 5880|
|AGCTAAAACC|ACTAGAATAC|GAGCCACAAT|AAATAAAGA|TTTTATTTAG|TTTCCAGAAA 5940|
|AAGGGGGGAA|TGAAAGACCC|CACCAAGTTG|CTTAGCCTGA|TGCCGCTGTA|ACGCCATTTT 6000|
|GCAAGGCATG|GAAAATACC|AAACCAAGAA|TAGAGAAGTT|CAGATCAAGG|GCGGGTACAT 6060|
|GAAAATAGCT|AACGTTGGGC|CAAACAGGAT|ATCTGCGGTG|AGCAGTTTCG|GCCCCGGCCC 6120|
|GGGGCAAGAA|CAGATGGTCA|CCGCAGTTTC|GGCCCCGGCC|CGAGGCAAG|AACAGATGGT 6180|
|CCCCAGATAT|GGCCCAACCC|TCAGCAGTTT|CTTAAGACCC|ATCAGATGTT|TCCAGGCTCC 6240|
|CCCAAGGACC|TGAAATGACC|CTGCGCCTTA|TTTGAATTAA|CCAATCAGCC|TGCTTCTCGC 6300|
|TTCTGTTCGC|GCGCTTCTGC|TTCCCGAGCT|CTATAAAAGA|GCTCACAACC|CCTCACTCGG 6360|
|CGCGCCAGTC|CTCCGATTGA|CTGAGTCGCC|CGGGTACCCG|TGTTCCCAAT|AAAGCCTCTT 6420|
|GCTGATTGCA|TCCGAATCGT|GGACTCGCTG|ATCCTTGGGA|GGGTCTCCTC|AGATTGATTG 6480|
|ACTGCCCACC|TGGGGGTCTT|TCAGT| | | 6505|

( 2 ) INFORMATION FOR SEQ ID NO: 6:

( i ) SEQUENCE CHARACTERISTICS:
        ( A ) LENGTH: 9318 base pairs
        ( B ) TYPE: nucleic acid
        ( C ) STRANDEDNESS: double
        ( D ) TOPOLOGY: circular ( i i ) MOLECULE TYPE: DNA ( x i ) SEQUENCE DESCRIPTION: SEQ ID NO: 6:

| | | | | | |
|---|---|---|---|---|---|
|TCGAGGGGGG|GCCCGGTACC|GATTAGTCCA|ATTTGTTAAA|GACAGGATAT|CAGGTGGTCC 60|
|AGGCTCTAGT|TTTGACTCAA|CAATATCACC|AGCTGAAGCC|TATAGAGTAC|GAGCCATAGA 120|
|TAGAATAAAA|GATTTTATTT|AGTCTCCAGA|AAAAGGGGGG|AATGAAAGAC|CCCACCTGTA 180|
|GGTTTGGCAA|GCTAGCTTAA|GTAACGCCAT|TTTGCAAGGC|ATGGAAAATA|CATAACTGAG 240|
|AATAGAGAAG|TTCAGATCAA|GGTTAGGAAC|AGAGAGACAG|CAGAATATGG|GCCAAACAGG 300|
|ATATCTGTGG|TAAGCAGTTC|CTGCCCCGCT|CAGGGCCAAG|AACAGATGGT|CCCCAGATGC 360|
|GGTCCCGCCC|TCAGCAGTTT|CTAGAGAACC|ATCAGATGTT|TCCAGGGTGC|CCCAAGGACC 420|
|TGAAAATGAC|CCTGTGCCTT|ATTTGAACTA|ACCAATCAGT|TCGCTTCTCG|CTTCTGTTCG 480|
|CGCGCTTCTG|CTCCCCGAGC|TCAATAAAAG|AGCCCACAAC|CCCTCACTCG|GCGCGCCAGT 540|
|CCTCCGATTG|ACTGCGTCGC|CCGGGTACCC|GTATTCCCAA|TAAAGCCTCT|TGCTGTTTGC 600|

```
ATCCGAATCG TGGACTCGCT GATCCTTGGG AGGGTCTCCT CAGATTGATT GACTGCCCAC    660
CTCGGGGGTC TTTCATTTGG AGGTTCCACC GAGATTTGGA GACCCCAGCC CAGGGACCAC    720
CGACCCCCCC GCCGGGAGGT AAGCTGGCCA GCGGTCGTTT CGTGTCTGTC TCTGTCTTTG    780
TGCGTGTTTG TGCCGGCATC TAATGTTTGC GCCTGCGTCT GTACTAGTTG GCTAACTAGA    840
TCTGTATCTG GCGGTCCGGC GGAAGAACTG ACGAGTTCGT ATTCCCGGCC GCAGCCCCTA    900
GGAGACGTCC CAGCGGCCTC GGGGGCCCGT TTTGTGGCCC GTTCTGTGTC GTTAACCACC    960
CGAGTCGGAC TTTTTGGAGC TCCGCCACTG TCCGAGGGGT ACGTGGCTTT GTTGGGGGAC   1020
GAGAGACAGA GACACTTCCC GCCCCGTCT GAATTTTGC TTTCGGTTTT ACGCCGAAAC    1080
CGCGCCGCGC GTCTTGTCTG CTGCAGCATC GTTCTGTGTT GTCTCTGTCT GACTGTGTTT   1140
CTGTATTTGT CTGAAAATTA GGGCCAGACT GTTACCACTC CCTTAAGTTT GACCTTAGAT   1200
CACTGGAAAG ATGTCGAGCG GATCGCTCAC AACCAGTCGG TAGATGTCAA GAAGAGACGA   1260
TGGGTTACCT TCTGCTCTGC AGAATGGCCA ACCTTTAACG TCGGATGGCC GCGAGACGGC   1320
ACCTTTAACC GAGACCTCAT CACCCAGGTT AAGATCAAGG TCTTTTCACC TGGCCCGCAT   1380
GGACACCCAG ACCAGGTCCC CTACATCGTG ACCTGGGAAG CCTTGGCTTT TGACCCCCCT   1440
CCCTGGGTCA AGCCCTTTGT ACACCCTAAG CCTCCGCCTC CTCTTCCTCC ATCCGCCCCG   1500
TCTCTCCCCC TTGAACCTCC TCTTTCGACC CCGCCTCGAT CCTCCCTTTA TCCAGCCCTC   1560
ACTCCTTCTC TAGGCGGCTC CACCGCGGTG GCGGCCGCTC TAGAACTAGT GGGATCCCGC   1620
CGCGGCGGGT ACCGAGCTCA TTCGAGTAGC GGCTCTTCCA AGCTCAAAGA AGCAGAGGCC   1680
GCTGTTCGTT TCCTTTAGGT CTTTCCACTA AAGTCGGAGT ATCTTCTTCC AAGATTTCAC   1740
GTCTTGGTGG CCGTTCCAAG GAGCGCGAGG TCGGGATGGA TCTTGAAGGG GACCGCAATG   1800
GAGGAGCAAA GAAGAAGAAC TTTTTTAAAC TGAACAATAA AAGTGAAAAA GATAAGAAGG   1860
AAAAGAAACC AACTGTCAGT GTATTTTCAA TGTTTCGCTA TTCAAATTGG CTTGACAAGT   1920
TGTATATGGT GGTGGGAACT TTGGCTGCCA TCATCCATGG GGCTGGACTT CCTCTCATGA   1980
TGCTGGTGTT TGGAGAAATG ACAGATATCT TTGCAAATGC AGGAAATTTA GAAGATCTGA   2040
TGTCAAACAT CACTAATAGA AGTGATATCA ATGATACAGG GTTCTTCATG AATCTGGAGG   2100
AAGACATGAC CAGGTATGCC TATTATTACA GTGGAATTGG TGCTGGGGTG CTGGTTGCTG   2160
CTTACATTCA GGTTTCATTT TGGTGCCTGG CAGCTGGAAG ACAAATACAC AAAATTAGAA   2220
AACAGTTTTT TCATGCTATA ATGCGACAGG AGATAGGCTG GTTTGATGTG CACGATGTTG   2280
GGGAGCTTAA CACCCGACTT ACAGATGATG TCTCTAAGAT TAATGAAGTT ATTGGTGACA   2340
AAATTGGAAT GTTCTTTCAG TCAATGGCAA CATTTTTCAC TGGGTTTATA GTAGGATTTA   2400
CACGTGGTTG GAAGCTAACC CTTGTGATTT TGGCCATCAG TCCTGTTCTT GGACTGTCAG   2460
CTGCTGTCTG GGCAAAGATA CTATCTTCAT TTACTGATAA AGAACTCTTA GCGTATGCAA   2520
AAGCTGGAGC AGTAGCTGAA GAGGTCTTGG CAGCAATTAG AACTGTGATT GCATTTGGAG   2580
GACAAAAGAA AGAACTTGAA AGGTACAACA AAAATTTAGA AGAAGCTAAA AGAATTGGGA   2640
TAAAGAAAGC TATTACAGCC AATATTTCTA TAGGTGCTGC TTTCCTGCTG ATCTATGCAT   2700
CTTATGCTCT GGCCTTCTGG TATGGGACCA CCTTGGTCCT CTCAGGGGAA TATTCTATTG   2760
GACAAGTACT CACTGTATTC TTTTCTGTAT TAATTGGGGC TTTTAGTGTT GGACAGGCAT   2820
CTCCAAGCAT TGAAGCATTT GCAAATGCAA GAGGAGCAGC TTATGAAATC TTCAAGATAA   2880
TTGATAATAA GCCAAGTATT GACAGCTATT CGAAGAGTGG GCACAAACCA GATAATATTA   2940
AGGGAAATTT GGAATTCAGA AATGTTCACT TCAGTTACCC ATCTCGAAAA GAAGTTAAGA   3000
```

```
TCTTGAAGGG  CCTGAACCTG  AAGGTGCAGA  GTGGGCAGAC  GGTGGCCCTG  GTTGGAAACA   3060

GTGGCTGTGG  GAAGAGCACA  ACAGTCCAGC  TGATGCAGAG  GCTCTATGAC  CCCACAGAGG   3120

GGATGGTCAG  TGTTGATGGA  CAGGATATTA  GGACCATAAA  TGTAAGGTTT  CTACGGGAAA   3180

TCATTGGTGT  GGTGAGTCAG  GAACCTGTAT  TGTTTGCCAC  CACGATAGCT  GAAAACATTC   3240

GCTATGGCCG  TGAAAATGTC  ACCATGGATG  AGATTGAGAA  AGCTGTCAAG  GAAGCCAATG   3300

CCTATGACTT  TATCATGAAA  CTGCCTCATA  AATTTGACAC  CCTGGTTGGA  GAGAGAGGGG   3360

CCCAGTTGAG  TGGTGGGCAG  AAGCAGAGGA  TCGCCATTGC  ACGTGCCCTG  GTTCGCAACC   3420

CCAAGATCCT  CCTGCTGGAT  GAGGCCACGT  CAGCCTTGGA  CACAGAAAGC  GAAGCAGTGG   3480

TTCAGGTGGC  TCTGGATAAG  GCCAGAAAAG  GTCGGACCAC  CATTGTGATA  GCTCATCGTT   3540

TGTCTACAGT  TCGTAATGCT  GACGTCATCG  CTGGTTTCGA  TGATGGAGTC  ATTGTGGAGA   3600

AAGGAAATCA  TGATGAACTC  ATGAAGAGA   AAGGCATTTA  CTTCAAACTT  GTCACAATGC   3660

AGACAGCAGG  AAATGAAGTT  GAATTAGAAA  ATGCAGCTGA  TGAATCCAAA  AGTGAAATTG   3720

ATGCCTTGGA  AATGTCTTCA  AATGATTCAA  GATCCAGTCT  AATAAGAAAA  AGATCAACTC   3780

GTAGGAGTGT  CCGTGGATCA  CAAGCCCAAG  ACAGAAAGCT  TAGTACCAAA  GAGGCTCTGG   3840

ATGAAAGTAT  ACCTCCAGTT  TCCTTTTGGA  GGATTATGAA  GCTAAATTTA  ACTGAATGGC   3900

CTTATTTTGT  TGTTGGTGTA  TTTTGTGCCA  TTATAAATGG  AGGCCTGCAA  CCAGCATTTG   3960

CAATAATATT  TTCAAAGATT  ATAGGGGTTT  TTACAAGAAT  TGATGATCCT  GAAACAAAAC   4020

GACAGAATAG  TAACTTGTTT  TCACTATTGT  TTCTAGCCCT  TGGAATTATT  TCTTTTATTA   4080

CATTTTTCCT  TCAGGGTTTC  ACATTTGGCA  AGCTGGAGA   GATCCTCACC  AAGCGGCTCC   4140

GATACATGGT  TTTCCGATCC  ATGCTCAGAC  AGGATGTGAG  TTGGTTTGAT  GACCCTAAAA   4200

ACACCACTGG  AGCATTGACT  ACCAGGCTCG  CCAATGATGC  TGCTCAAGTT  AAAGGGGCTA   4260

TAGGTTCCAG  GCTTGCTGTA  ATTACCCAGA  ATATAGCAAA  TCTTGGGACA  GGAATAATTA   4320

TATCCTTCAT  CTATGGTTGG  CAACTAACAC  TGTTACTCTT  AGCAATTGTA  CCCATCATTG   4380

CAATAGCAGG  AGTTGTTGAA  ATGAAAATGT  TGTCTGGACA  AGCACTGAAA  GATAAGAAAG   4440

AACTAGAAGG  TGCTGGGAAG  ATCGCTACTG  AAGCAATAGA  AAACTTCCGA  ACCGTTGTTT   4500

CTTTGACTCA  GGAGCAGAAG  TTTGAACATA  TGTATGCTCA  GAGTTTGCAG  GTACCATACA   4560

GAAACTCTTT  GAGGAAAGCA  CACATCTTTG  GAATTACATT  TTCCTTCACC  CAGGCAATGA   4620

TGTATTTTTC  CTATGCTGGA  TGTTTCCGGT  TTGGAGCCTA  CTTGGTGGCA  CATAAACTCA   4680

TGAGCTTTGA  GGATGTTCTG  TTAGTATTTT  CAGCTGTTGT  CTTTGGTGCC  ATGGCCGTGG   4740

GGCAAGTCAG  TTCATTTGCT  CCTGACTATG  CCAAAGCCAA  AATATCAGCA  GCCCACATCA   4800

TCATGATCAT  TGAAAAAACC  CCTTTGATTG  ACAGCTACAG  CACGGAAGGC  CTAATGCCGA   4860

ACACATTGGA  AGGAAATGTC  ACATTGGTG   AAGTTGTATT  CAACTATCCC  ACCCGACCGG   4920

ACATCCCAGT  GCTTCAGGGA  CTGAGCCTGG  AGGTGAAGAA  GGGCCAGACG  CTGGCTCTGG   4980

TGGGCAGCAG  TGGCTGTGGG  AAGAGCACAG  TGGTCCAGCT  CCTGGAGCGG  TTCTACGACC   5040

CCTTGGCAGG  GAAAGTGCTG  CTTGATGGCA  AAGAAATAAA  GCGACTGAAT  GTTCAGTGGC   5100

TCCGAGCACA  CCTGGGCATC  GTGTCCCAGG  AGCCCATCCT  GTTTGACTGC  AGCATTGCTG   5160

AGAACATTGC  CTATGGAGAC  AACAGCCGGG  TGGTGTCACA  GGAAGAGATC  GTGAGGGCAG   5220

CAAAGGAGGC  CAACATACAT  GCCTTCATCG  AGTCACTGCC  TAATAAATAT  AGCACTAAAG   5280

TAGGAGACAA  AGGAACTCAG  CTCTCTGGTG  GCCAGAAACA  ACGCATTGCC  ATAGCTCGTG   5340

CCCTTGTTAG  ACAGCCTCAT  ATTTTGCTTT  TGGATGAAGC  CACGTCAGCT  CTGGATACAG   5400
```

```
AAAGTGAAAA GGTTGTCCAA GAAGCCCTGG ACAAAGCCAG AGAAGGCCGC ACCTGCATTG     5460
TGATTGCTCA CCGCCTGTCC ACCATCCAGA ATGCAGACTT AATAGTGGTG TTTCAGAATG     5520
GCAGAGTCAA GGAGCATGGC ACGCATCAGC AGCTGCTGGC ACAGAAAGGC ATCTATTTTT     5580
CAATGGTCAG TGTCCAGGCT GGAACAAAGC GCCAGTGAAC TCTGACTGTA TGAGATGTTA     5640
AATACTTTTT AATGGGGATC CCCCGGGCTG CAGGAATTCG ATATCAAGCT TATCGATACC     5700
GTCGACCTCG AGGGGGGGCC CGGTACAGAT TAGTCCAATT TGTTAAAGAC AGGATATCAG     5760
GTGGTCCAGG CTCTAGTTTT GACTCAACAA TATCACCAGC TGAAGCCTAT AGAGTACGAG     5820
CCATAGATAG AATAAAAGAT TTTATTTAGT CTCCAGAAAA AGGGGGGAAT GAAAGACCCC     5880
ACCTGTAGGT TTGGCAAGGC TAGCTTAAGT AAGCCATTTT GCAAGGCATG GAAAATACA     5940
TAACTGAGAA TAGAGAAGTT CAGATCAAGG TTAGGAACAG AGAGACAGGA GAATATGGGC     6000
CAAACAGGAT ATCTGTGGTA AGCAGTTCCT GCCCCGGCTC AGGGCCAAGA ACAGTTGGAA     6060
CAGCAGAATA TGGGCCAAAC AGGATATCTG TGGTAAGCAG TTCCTGCCCC GGCTCAGGGC     6120
CAAGAACAGA TGGTCCCCAG ATGCGGTCCC GCCCTCAGCA GTTTCTAGAG AACCATCAGA     6180
TGTTTCCAGG GTGCCCCAAG GACCTGAAAT GACCCTGTGC CTTATTTGAA CTAACCAATC     6240
AGTTCGCTTC TCGCTTCTGT TCGCGCGCTT CTGCTCCCCG AGCTCAATAA AAGAGCCCAC     6300
AACCCCTCAC TCGGCGCGCC AGTCCTCCGA TAGACTGCGT CGCCCGGGTA CCCGTATTCC     6360
CAATAAAGCC TCTTGCTGTT TGCATCCGAA TCGTGGACTC GCTGATCCTT GGGAGGGTCT     6420
CCTCAGATTG ATTGACTGCC CACCTCGGGG GTCTTTCAGT AGGATCTGA CCGATGCCCT     6480
TGAGAGCCTT CAACCCAGTC AGCTCCTTCC GGTGGGCGCG GGGCATGACT ATCGTCGCCG     6540
CACTTATGAC TGTCTTCTTT ATCATGCAAC TCGTAGGACA GGTGCCGGCA GCGCTCTGGG     6600
TCATTTTCGG CGAGGACCGC TTTCGCTGGA GCGCGACGAT GATCGGCCTG TCGCTTGCGG     6660
TATTCGGAAT CTTGCACGCC CTCGCTCAAG CCTTCGTCAC TGGTCCCGCC ACCAAACGTT     6720
TCGGCGAGAA GCAGGCCATT ATCGCCGGCA TGGCGGCCGA CGCGCTGGGC TACGTCTTGC     6780
TGGCGTTCGC GACGCGAGGC TGGATGGCCT TCCCCATTAT GATTCTTCTC GCTTCCGGCG     6840
GCATCGGGAT GCCCGCGTTG CAGGCCATGC TGTCCAGGCA GGTAGATGAC GACCATCAGG     6900
GACAGCTTCA AGGATCGCTC GCGGCTCTTA CCAGCCTAAC TTCGATCACT GGACCGCTGA     6960
TCGTCACGGC GATTTATGCC GCCTCGGCGA GCACATGGAA CGGGTTGGCA TGGATTGTAG     7020
GCGCCTGATG CGGTATTTTC TCCTTACGCA TCTGTGCGGT ATTTCACACC GCATATGGTG     7080
CACTCTCAGT ACAATCTGCT CTGATGCCGC ATAGTTAAGC CAGCCCCGAC ACCCGCCAAC     7140
ACCCGCTGAC GCGCCCTGAC GGGCTTGTCT GCTCCCGGCA TCCGCTTACA GACAAGCTGT     7200
GACCGTCTCC GGGAGCTGCA TGTGTCAGAG GTTTTCACCG TCATCACCGA AACGCGCGAG     7260
ACGAAAGGGC CTCGTGATAC GCCTATTTTT ATAGGTTAAT GTCATGATAA TAATGGTTTC     7320
TTAGACGTCA GGTGGCACTT TTCGGGGAAA TGTGCGCGGA ACCCCTATTT GTTTATTTTT     7380
CTAAATACAT TCAAATATGT ATCCGCTCAT GAGACAATAA CCCTGATAAA TGCTTCAATA     7440
ATATTGAAAA AGGAAGAGTA TGAGTATTCA ACATTTCCGT GTCGCCCTTA TTCCCTTTTT     7500
TGCGGCATTT TGCCTTCCTG TTTTTGCTCA CCCAGAAACG CTGGTGAAAG TAAAAGATGC     7560
TGAAGATCAG TTGGGTGCAC GAGTGGGTTA CATCGAACTG GATCTCAACA GCGGTAAGAT     7620
CCTTGAGAGT TTTCGCCCCG AAGAACGTTT TCCAATGATG AGCACTTTTA AAGTTCTGCT     7680
ATGTGGCGCG GTATTATCCC GTATTGACGC CGGGCAAGAG CAACTCGGTC GCCGCATACA     7740
CTATTCTCAG AATGACTTGG TTGAGTACTC ACCAGTCACA GAAAAGCATC TTACGGATGG     7800
```

-continued

| | | | | | | |
|---|---|---|---|---|---|---|
| CATGACAGTA | AGAGAATTAT | GCAGTGCTGC | CATAACCATG | AGTGATAACA | CTGCGGCCAA | 7860 |
| CTTACTTCTG | ACAACGATCG | GAGGACCGAA | GGAGCTAACC | GCTTTTTTGC | ACAACATGGG | 7920 |
| GGATCATGTA | ACTCGCCTTG | ATCGTTGGGA | ACCGGAGCTG | AATGAAGCCA | TACCAAACGA | 7980 |
| CGAGCGTGAC | ACCACGATGC | CTGTAGCAAT | GGCAACAACG | TTGCGCAAAC | TATTAACTGG | 8040 |
| CGAACTACTT | ACTCTAGCTT | CCCGGCAACA | ATTAATAGAC | TGGATGGAGG | CGGATAAAGT | 8100 |
| TGCAGGACCA | CTTCTGCGCT | CGGCCCTTCC | GGCTGGCTGG | TTTATTGCTG | ATAAATCTGG | 8160 |
| AGCCGGTGAG | CGTGGGTCTC | GCGGTATCAT | TGCAGCACTG | GGGCCAGATG | GTAAGCCCTC | 8220 |
| CCGTATCGTA | GTTATCTACA | CGACGGGGAG | TCAGGCAACT | ATGGATGAAC | GAAATAGACA | 8280 |
| GATCGCTGAG | ATAGGTGCCT | CACTGATTAA | GCATTGGTAA | CTGTCAGACC | AAGTTTACTC | 8340 |
| ATATATACTT | TAGATTGATT | TAAAACTTCA | TTTTTAATTT | AAAAGGATCT | AGGTGAAGAT | 8400 |
| CCTTTTTGAT | AATCTCATGA | CCAAAATCCC | TTAACGTGAG | TTTTCGTTCC | ACTGAGCGTC | 8460 |
| AGACCCCGTA | GAAAAGATCA | AAGGATCTTC | TTGAGATCCT | TTTTTTCTGC | GCGTAATCTG | 8520 |
| CTGCTTGCAA | ACAAAAAAAC | CACCGCTACC | AGCGGTGGTT | TGTTTGCCGG | ATCAAGAGCT | 8580 |
| ACCAACTCTT | TTTCCGAAGG | TAACTGGCTT | CAGCAGAGCG | CAGATACCAA | ATACTGTCCT | 8640 |
| TCTAGTGTAG | CCGTAGTTAG | GCCACCACTT | CAAGAACTCT | GTAGCACCGC | CTACATACCT | 8700 |
| CGCTCTGCTA | ATCCTGTTAC | CAGTGGCTGC | TGCCAGTGGC | GATAAGTCGT | GTCTTACCGG | 8760 |
| GTTGGACTCA | AGACGATAGT | TACCGGATAA | GGCGCAGCGG | TCGGGCTGAA | CGGGGGGTTC | 8820 |
| GTGCACACAG | CCCAGCTTGG | AGCGAACGAC | CTACACCGAA | CTGAGATACC | TACAGCGTGA | 8880 |
| GCATTGAGAA | AGCGCCACGC | TTCCCGAAGG | GAGAAAGGCG | GACAGGTATC | CGGTAAGCGG | 8940 |
| CAGGGTCGGA | ACAGGAGAGC | GCACGAGGGA | GCTTCCAGGG | GGAAACGCCT | GGTATCTTTA | 9000 |
| TAGTCCTGTC | GGGTTTCGCC | ACCTCTGACT | TGAGCGTCGA | TTTTTGTGAT | GCTCGTCAGG | 9060 |
| GGGGCGGAGC | CTATGGAAAA | ACGCCAGCAA | CGCGGCCTTT | TTACGGTTCC | TGGCCTTTTG | 9120 |
| CTGGCCTTTT | GCTCACATGT | TCTTTCCTGC | GTTATCCCCT | GATTCTGTGG | ATAACCGTAT | 9180 |
| TACCGCCTTT | GAGTGAGCTG | ATACCGCTCG | CCGCAGCCGA | ACGACCGAGC | GCAGCGAGTC | 9240 |
| AGTGAGCGAG | GAAGCGGAAG | AGCGCCCAAT | ACGCAAACCG | CCTCTCCCCG | CGCGTTGGCC | 9300 |
| GATTCATTAA | TGCAGNNG | | | | | 9318 |